US008338142B2

(12) United States Patent
Mori et al.

(10) Patent No.: US 8,338,142 B2
(45) Date of Patent: Dec. 25, 2012

(54) METHOD FOR PRODUCING OPTICALLY ACTIVE 3-AMINOPIPERIDINE OR SALT THEREOF

(75) Inventors: Kohei Mori, Takasago (JP); Masutoshi Nojiri, Takasago (JP); Akira Nishiyama, Takasago (JP); Naoaki Taoka, Takasago (JP)

(73) Assignee: Kaneka Corporation, Osaka (JP)

( * ) Notice: Subject to any disclaimer, the term of this patent is extended or adjusted under 35 U.S.C. 154(b) by 399 days.

(21) Appl. No.: 12/449,645

(22) PCT Filed: Feb. 18, 2008

(86) PCT No.: PCT/JP2008/052618
§ 371 (c)(1),
(2), (4) Date: Aug. 19, 2009

(87) PCT Pub. No.: WO2008/102720
PCT Pub. Date: Aug. 28, 2008

(65) Prior Publication Data
US 2010/0105917 A1    Apr. 29, 2010

(30) Foreign Application Priority Data
Feb. 19, 2007    (JP) .................... 2007-037598

(51) Int. Cl.
*C12P 17/12*    (2006.01)
(52) U.S. Cl. ...................... 435/122; 546/245
(58) Field of Classification Search .............. 435/122; 546/245
See application file for complete search history.

(56) References Cited

U.S. PATENT DOCUMENTS

| 5,622,846 | A | 4/1997 | Kiener et al. | |
| 5,726,188 | A | 3/1998 | Takano et al. | |
| 5,766,893 | A | 6/1998 | Kiener et al. | |
| 6,214,604 | B1 | 4/2001 | Kiener et al. | |
| 6,218,156 | B1 | 4/2001 | Yasohara et al. | |
| 6,777,224 | B2 * | 8/2004 | Mitsuhashi et al. | 435/280 |
| 2001/0055798 | A1 * | 12/2001 | Hansen et al. | 435/280 |
| 2002/0137153 | A1 * | 9/2002 | Ramer et al. | 435/129 |

FOREIGN PATENT DOCUMENTS

| JP | 7-133273 | 5/1995 |
| JP | 7-330732 | 12/1995 |
| JP | 8-56652 | 3/1996 |
| JP | 10-127280 | 5/1998 |
| JP | 11-508761 | 8/1999 |
| JP | 2002-371060 | 12/2002 |
| JP | 2004-105152 | 4/2004 |
| JP | 2007117034 A * | 5/2007 |
| WO | WO 9201062 A1 * | 1/1992 |
| WO | 98/35025 | 8/1998 |
| WO | 01/68604 | 9/2001 |
| WO | 03/004496 | 1/2003 |
| WO | WO 2006084470 A2 * | 8/2006 |

OTHER PUBLICATIONS

Machine translation of [Detailed Description] of JP 2004-105152 A online "http://www4.ipdl.inpit.go.jp/cgi-bin/tran_web_cgi_ejje?atw_u=http%3A%2F%2Fwww4.ip" accessed Dec. 1, 2011.*

Hirrlinger et. al. "Purification and Properties of an Amidase from *Rhodococcus erythropolis* MP50 Which Enantioselectively Hydrolyzes 2-Arylpropionamides" Journal of Bacteriology, Jun. 1996, p. 3501-3507.*
Komeda et. al. "S-Stereoselective piperazine-2-tert-butylcarboxamide hydrolase from *Pseudomonas azotoformans* IAM 1603 is a novel L-amino acid amidase" Eur. J. Biochem. 2004271, 1465-1475.*
Kotlova et. al. "Isolation and Primary Characterization of an Amidase from *Rhodococcus rhodochrous*" Biochemistry (Moscow), vol. 64, No. 4, 1999, pp. 384-389.*
Komeda, Hidenobu, et al., "A novel *R*-stereoselective amidase from *Pseudomonas* sp. MCI3434 acting on piperazine-2-*tert*-butylcarboxamide", Eur. J. Biochem., vol. 271, 2004, pp. 1580-1590.
International Search Report dated Mar. 18, 2008 in the International (PCT) Application PCT/JP2008/052618 of which the present application is the U.S. National Stage.
Hidenobu Komeda et al., "A novel *R*-stereoselective amidase from *Pseudomonas* sp. MCI3434 acting on piperazine-2-*tert*-butylcarboxamide", Eur. J. Biochem., vol. 271, No. 8, pp. 1580-1590, 2004.
Klaus Weber et al., "Enantiopure 4- and 5-Aminopiperidin-2-ones: Regiocontrolled Synthesis and Conformational Characterization as Bioactive β-Turn Mimetics", J. Org. Chem., 65, pp. 7406-7416, 2000.
Sung-Hwan Moon et al., "An Efficient Conversion of Chiral α-Amino Acids to Enantiomerically Pure 3-Amino Cyclic Amines", Synthetic Communications, 28(21), pp. 3919-3926, 1998.
Kazuo Miyamura et al., "Reactions of Copper (II) Complexes of Optically Active *N*-Substituted Diamines with Alk-3-en-2-ones or 4-Hydroxyalkan-2-ones: Formation of Optically Active Macrocycles", J. Chem. Soc. Dalton Trans., pp. 1127-1132, 1987.
Hidenobu Komeda et al., "S-Stereoselective piperazine-2-*tert*-butylcarboxamide hydrolase from *Pseudomonas azotoformans* IAM 1603 is a novel L-amino acid amidase", Eur. J. Biochem., vol. 271, No. 8, pp. 1465-1475, 2004.
International Preliminary Report on Patentability together with translation of PCT Written Opinion issued Aug. 27, 2009 for International (PCT) Application No. PCT/JP2008/052618 on which the present U.S. application is based.
Extended European Search Report issued Sep. 26, 2012 in corresponding European Application No. 08711442.7.
Jean, Ludovic, et al., "A convenient route to 1-benzyl 3-aminopyrrolidine and 3-aminopiperidine", Tetrahedron Letters, vol. 42, 2001, pp. 5645-5649.

* cited by examiner

*Primary Examiner* — David K O'Dell
(74) *Attorney, Agent, or Firm* — Wenderoth, Lind & Ponack, L.L.P.

(57) ABSTRACT

The present invention relates to a method for producing an optically active 3-aminopiperidine or salt thereof. In the method, a racemic nipecotamide is stereoselectively hydrolyzed to obtain an optically active nipecotamide and an optically active nipecotic acid in the presence of an enzyme source derived from an organism, and then the optically active nipecotamide is derived into an optically active aminopiperidine or salt thereof by aroylation, Hofmann rearrangement, deprotection of the amino group and further deprotection; or the optically active nipecotamide is derived into an optically active aminopiperidine or salt thereof by selective protection with BOC, Hofmann rearrangement and further deprotection. It is possible by the present invention to produce an optically active 3-aminopiperidine or salt thereof useful as a pharmaceutical intermediate from an inexpensive and easily available starting material by easy method applicable to industrial manufacturing.

13 Claims, No Drawings

METHOD FOR PRODUCING OPTICALLY ACTIVE 3-AMINOPIPERIDINE OR SALT THEREOF

TECHNICAL FIELD

The present invention relates to a method for producing an optically active 3-aminopiperidine or salt thereof useful as a pharmaceutical intermediate, and to intermediates useful for producing the 3-aminopiperidine.

BACKGROUND ART

As methods for producing an optically active 3-aminopiperidine or salt thereof, or a derivative of optically active 3-aminopiperidine, for example, the following methods are known:

1) a method, wherein L-ornithine monohydrochloride is methyl-esterified, and then (S)-3-amino piperidone is obtained by chromatography with an ion exchange resin, the (S)-3-amino piperidone is reacted with lithium aluminum hydride to be (S)-3-aminopiperidine, an inorganic salt is removed by filtration, and the target compound is purified (Non-patent Document 1);

2) a method, wherein ethyl nipecotate is optically resolved using L-tartaric acid, the nitrogen atom is protected with benzyloxycarbonyl group, the ethyl ester is hydrolyzed in alkaline condition, Curtius rearrangement is carried out using diphenylphosphoryl azide, the resulting isocyanate is reacted with tert-butanol to obtain (R)-1-(benzyloxycarbonyl)-3-(tert-butoxy carbonylamino)piperidine, and finally the benzyloxycarbonyl group is removed to produce (R)-3-(tert-butoxycarbonylamino)piperidine (Patent Document 1);

3) a method, wherein ethyl nipecotate is optically resolved using L-tartaric acid and the nitrogen atom is protected with benzyloxycarbonyl group as similar to the method 2), and then the ethyl ester is converted into an amide using ammonia, and subsequently Hofmann rearrangement is carried out to produce (R)-1-benzyl-3-aminopiperidine (Patent Document 2);

4) a method, wherein an (R)-1-(tert-butoxycarbonyl)nipecotic anhydride with other acid is reacted with sodium azide to produce a carboxylic azide derivative, then Curtius rearrangement is carried out to obtain (R)-1-tert-butoxycarbonyl-3-(benzyloxy carbonylamino)piperidine, and deprotection is carried out at the 3-position to produce (R)-1-(tert-butoxycarbonyl)-3-amino piperidine (Patent Document 3);

5) a method, wherein a racemic 1-benzyl-3-aminopiperidine is optically resolved using dibenzoyl-D-tartaric acid to produce (S)-1-benzyl-3-aminopiperidine (Patent Document 4);

6) a method, wherein the amino group of L-aspartic acid is protected, the carboxy group is reduced, the resulting hydroxyl group is converted into a leaving group, the leaving group is replaced by potassium phthalimide and lithium cyanide, the phthalimide is hydrolyzed to obtain (S)-3-(N,N-dibenzylamino) piperidone, and finally the piperidone is reduced with lithium aluminum hydride to produce (S)-3-(N,N-dibenzylamino)piperidine (Non-patent Document 2);

7) a method, wherein the amino group of L-aspartic acid is protected, the carboxy group is reduced, the resulting hydroxyl group is converted into a leaving group, the resultant is reacted with ammonia to produce (S)-3-(tert-butoxycarbonyloxyamino) piperidine, the piperidine is reacted with benzylamine instead of ammonia to obtain (S)-1-benzyl-3-(tert-butoxycarbonyloxyamino) piperidine, and deprotection is carried out using trifluoroacetic acid to produce (S)-1-benzyl-3-aminopiperidine (Non-patent Document 3).

However, the method of conventional art 1) is problematic and impractical, since chromatography that is disadvantageous in industrial production and lithium aluminum hydride that is expensive and highly dangerous have to be used.

By the methods of conventional arts 2) to 7), a protected optically active 3-aminopiperidine can be produced, and an optically active 3-aminopiperidine can be produced by deprotecting the protected 3-aminopiperidine. However, the methods have the following problems.

The methods of conventional arts 2) and 4) have a serious problem for industrial implementation, since a reaction that utilizes an azide compound exhibiting an explosion risk, i.e. Curtius rearrangement, has to be carried out.

The productivity by the method of conventional art 3) is low, since yields of benzylation and Hofmann rearrangement process are low.

The starting material of the method of conventional art 5) is not easily available, and a multistep synthetic reaction is needed to obtain the starting material. In addition, expensive dibenzoyl-D-tartaric acid has to be used as an optical resolving agent.

The method of conventional art 6) art has problems both in safety and economical efficiency, since the number of the steps is large, and a highly toxic cyanide compound and an expensive reducing agent have to be used.

The method of conventional art 7) is also not advantageous in industrial production, since the number of the steps is large.

As mentioned above, all the presently known methods for producing an optically active 3-aminopiperidine or salt thereof or derivative thereof have problems in economical efficiency and safety or productivity; and thus, the methods are not practical for industrial implementation.

Patent Document 1: WO03/004496
Patent Document 2: JP7-133273A
Patent Document 3: WO01/068604
Patent Document 4: JP7-330732A
Non-patent Document 1: J. Chem. Soc. DALTON TRANS, 1987, 1127-1132
Non-patent Document 2: J. Org. Chem., 2000, 65, 7406-7416
Non-patent Document 3: Synthetic Communications, 1998, 28, 3919-3926

DISCLOSURE OF THE INVENTION

Problems to be Solved by the Invention

Under the above mentioned situation, the objective of the present invention is to provide a practical method for industrial production that can simply and easily produce an optically active 3-aminopiperidine or salt thereof useful as a pharmaceutical intermediate from an inexpensive readily available raw material, and intermediates useful for producing the optically active 3-aminopiperidine or salt thereof.

Means for Solving the Problems

The present inventors have intensely studied in consideration of the above; as a result, the inventors developed a method for simply and easily producing an optically active 3-aminopiperidine or salt thereof useful as a pharmaceutical intermediate from an inexpensive and readily available raw material.

The present invention relate to a method for producing an optically active nipecotamide derivative or an optically active nipecotin derivative, comprising steps of:

stereoselectively hydrolyzing a racemic nipecotamide derivative represented by the following formula (1):

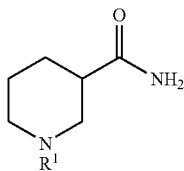
(1)

wherein, $R^1$ represents a hydrogen atom or a benzyl group, by using an enzyme source having ability to stereoselectively hydrolyze the racemic nipecotamide derivative (1), to convert the racemic nipecotamide derivative (1) into a mixture of an optically active nipecotamide derivative represented by the following formula (2):

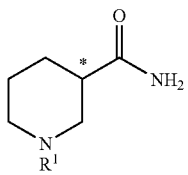
(2)

wherein, * indicates an asymmetric carbon atom; and $R^1$ means the same as the above,
and an optically active nipecotin derivative represented by the following formula (3):

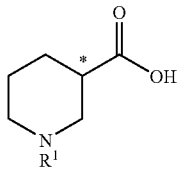
(3)

wherein, * and $R^1$ mean the same as the above;
and then isolating the optically active nipecotamide derivative (2) or the optically active nipecotin derivative (3) from the mixture.

Further, the present invention relates to a method for producing an optically active 1-aroyl-3-(protected amino)piperidine derivative, comprising steps of:

aroylating optically active nipecotamide represented by the following formula (2'):

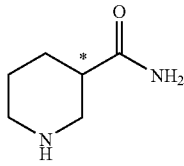
(2')

wherein, * indicates an asymmetric carbon atom, to produce an optically active 1-aroylnipecotamide derivative represented by the following formula (4):

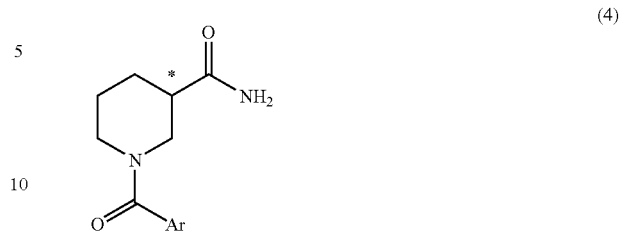
(4)

wherein, * indicates an asymmetric carbon atom; Ar represents an optionally substituted aryl group having 6 to 15 carbon atoms;

and then producing an optically active 1-aroyl-3-aminopiperidine derivative represented by the following formula (5):

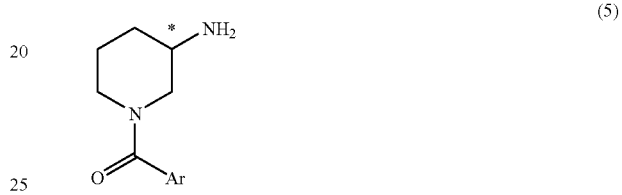
(5)

wherein, * and Ar mean the same as the above,
by Hofmann rearrangement at the amide group;
and further aroylating or carbamating the amino group for crystallization or extraction to isolate the optically active 1-aroyl-3-(protected amino)piperidine derivative represented by the following formula (6):

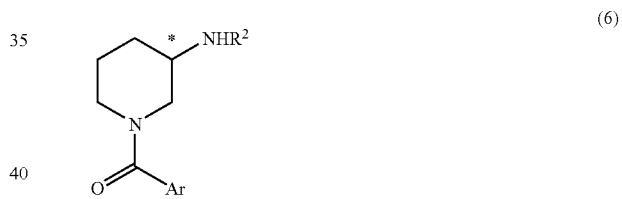
(6)

wherein, * and Ar mean the same as the above; $R^2$ represents an optionally substituted aroyl group having 7 to 15 carbon atoms, an alkyloxycarbonyl group having 2 to 15 carbon atoms, an alkenyloxycarbonyl group having 3 to 15 carbon atoms, an aryloxycarbonyl group having 7 to 15 carbon atoms, or an aralkyloxycarbonyl group having 8 to 15 carbon atoms.

Furthermore, the present invention relates to an optically active 1-aroylnipecotamide derivative represented by the following formula (4):

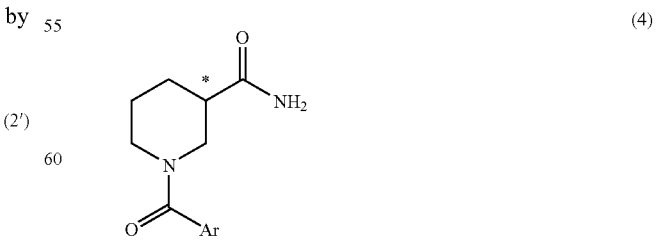
(4)

wherein, * indicates an asymmetric carbon atom; Ar represents a phenyl group, a p-methylphenyl group or a p-chlorophenyl group.

The present invention also relates to an optically active 1-aroyl-3-aminopiperidine derivative represented by the following formula (5):

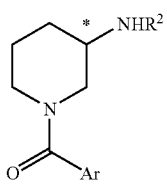
(5)

wherein, * indicates an asymmetric carbon atom; Ar represents a phenyl group, a p-methylphenyl group or a p-chlorophenyl group.

Further, the present invention relates to an optically active 1-aroyl-3-(protected amino)piperidine derivative represented by the following formula (6):

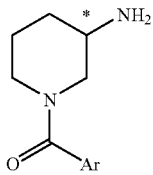
(6)

wherein, * indicates an asymmetric carbon atom; Ar represents a phenyl group, a p-methylphenyl group or a p-chlorophenyl group; $R^2$ represents a benzoyl group, a p-methylbenzoyl group, a p-chlorobenzoyl group or a tert-butoxycarbonyl group.

EFFECT OF THE INVENTION

According to the method of the present invention, it is possible to simply and easily produce an optically active 3-aminopiperidine or salt thereof useful as a pharmaceutical intermediate, and intermediates useful for producing the 3-aminopiperidine, from an inexpensive and readily available raw material.

BEST MODE FOR CARRYING OUT THE INVENTION

The outline of the present invention can be shown by the following scheme.

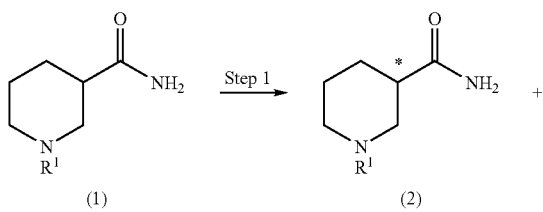

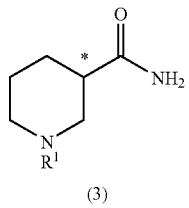
(3)

When $R^1$ is a hydrogen atom.

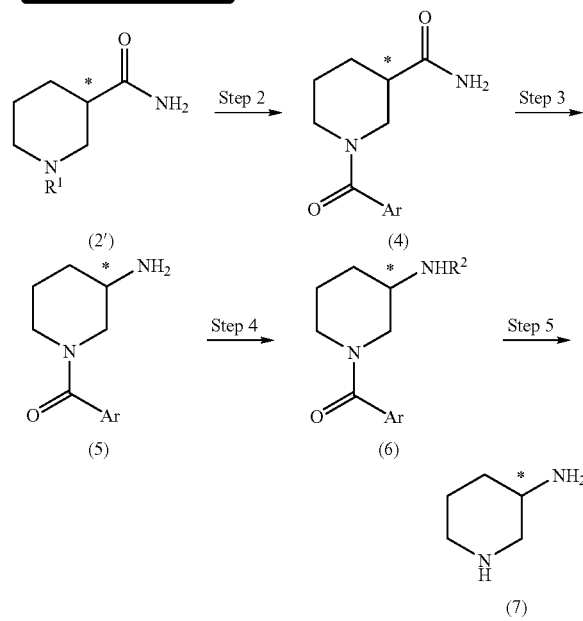

The present invention is described below for every step in order.

Step 1

In the present step, a racemic nipecotamide derivative represented by the following formula (1):

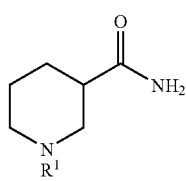
(1)

wherein, $R^1$ represents a hydrogen atom or a benzyl group, is stereoselectively hydrolyzed by using an enzyme source having an ability to stereoselectively hydrolyze the racemic nipecotamide derivative (1), to convert the racemic nipecotamide derivative (1) into a mixture of an optically active nipecotamide derivative represented by the following formula (2):

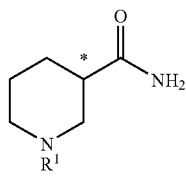
(2)

wherein, * indicates an asymmetric carbon atom; and $R^1$ means the same as the above, and an optically active nipecotin derivative represented by the following formula (3):

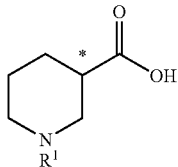

(3)

wherein, * and R¹ mean the same as the above;
and then the optically active nipecotamide derivative (2) or the optically active nipecotin derivative (3) is isolated from the mixture.

In the present invention, the "enzyme source" includes not only an enzyme having the above hydrolysis activity, but also a culture of a microorganism having the hydrolysis activity and processed product thereof. The "culture of a microorganism" means a bacterial cell-containing culture solution or a cultured bacterial cell; and the "processed product thereof" means, for example, a crude extract, a freeze-dried microbiality, an acetone-dried microbiality, a ground product of the bacterial cell, or the like, and includes such products so long as the products have the hydrolysis activity. In addition, the enzyme source can be immobilized by well-known means and be used as an immobilized enzyme or an immobilized mycelium. The immobilization can be carried out by a method known to those skilled in the art, such as crosslinking, physical adsorption and entrapment.

The each microorganism described below in the specification is available from International Patent Organism Depositary and other research institutions. For example, microorganisms specified by the NBRC number are available from National BioResource Project Chrysanthemum; microorganisms specified by the FERM number are available from International Patent Organism Depositary, National Institute of Advanced Industrial Science and Technology; microorganisms specified by the IAM number are available from The University of Tokyo Center for Bioinformatics; and microorganisms specified by the JCM number are available from RIKEN BioResource Center-Japan Collection of Microorganisms.

In the present step, the enzyme source having the ability to stereoselectively hydrolyze the racemic nipecotamide derivative (1) is not limited; however, is derived from, for example, a microorganism belonging to genus *Achromobacter, Brevibacterium, Cupriavidus, Pectobacterium, Pseudomonas, Rhodococcus* or *Staphylococcus*.

As the enzyme source having the ability to stereoselectively hydrolyze the S-enantiomer of the nipecotamide derivative, the enzyme source derived from the microorganism belonging to genus *Achromobacter, Cupriavidus, Pseudomonas* and *Rhodococcus* are exemplified.

As such an enzyme source, the enzyme sources derived from a microorganism selected from the group consisting of *Achromobacter xylosoxidans* subsp. *xylosoxidans, Cupriavidus* sp., *Pseudomonas chlororaphis* and *Rhodococcus erythropolis* are preferably exemplified; and the microorganism is more preferably *Achromobacter xylosoxidans* subsp. *Xylosoxidans* NBRC13495, *Cupriavidus* sp. KNK-J915 (FERN BP-10739), *Pseudomonas chlororaphis* NBRC3904 or *Rhodococcus erythropolis* IAM1440.

As the enzyme source having the ability to stereoselectively hydrolyze the R-enantiomer of the racemic nipecotamide derivative, the enzyme source derived from the microorganism belonging to genus *Brevibacterium, Pseudomonas, Pectobacterium* or *Staphylococcus* is exemplified.

As such an enzyme source, the enzyme source derived from a microorganism selected from the group consisting of *Brevibacterium iodinum, Pseudomonas fragi, Pectobacterium carotovorum* subsp. *carotovorum* and *Staphylococcus epidermidis* are preferably exemplified; and the microorganism is more preferably *Brevibacterium iodinum* NBRC3558, *Pseudomonas fragi* NBRC3458, *Pectobabterium carotovorum* subsp. *Carotovorum* NBRC12380 or *Staphylococcus epidermidis* JCM2414.

Either a wild-type strain or a variant strain may be used as the microorganism having the productivity of the hydrolase. Alternatively, a microorganism induced by genetic techniques such as cell fusion or gene manipulation can also be used. The microorganism that produces such a gene-engineered enzyme can be obtained by method, for example, including a step of isolating and/or purifying an enzyme to determine a part of or all the amino acid sequences of the enzyme, a step of obtaining the DNA sequence encoding the enzyme on the basis of the amino acid sequence, a step of introducing the DNA into another microorganism to obtain a recombinant microorganism, and a step of cultivating the recombinant microorganism to obtain the enzyme, as described in WO98/35025; or the like. The recombinant microorganism as described above includes a microorganism transformed by the plasmid having DNA that encodes the hydrolase. In addition, *Escherichia coli* is preferred as a host microorganism.

The culture medium for the microorganism used as the enzyme source is not particularly limited as long as the microorganism can grow. For example, a usual liquid media can be used that contain glucides such as glucose and sucrose, alcohols such as ethanol and glycerol, fatty acids such as oleic acid and stearic acid and esters thereof, and oils such as rapeseed oil and soybean oil, and the like, as carbon sources; ammonium sulfate, sodium nitrate, peptone, casamino acid, corn steep liquor, bran, yeast extract, and the like, as nitrogen sources; magnesium sulfate, sodium chloride, calcium carbonate, potassium monohydrogen phosphate, potassium dihydrogen phosphate, and the like, as inorganic salts; malt extract, meat extract, and the like, as other nutrient sources. In addition, an inducer may be added to the medium for inducing the enzyme production of microorganism.

The inducer includes nitrile, lactam compound, amide, and the like. The example of the nitrile includes acetonitrile, isovaleronitrile, propionitrile, pivalonitrile, n-butyronitrile, isobutyronitrile, n-capronitrile, 3-pentenenitrile, and the like; the example of the lactam compound includes γ-butyrolactam, δ-valerolactam, ε-caprolactam, and the like; and the example of the amide includes crotonamide, benzamide, propionamide, acetamide, n-butyl amide, isobutylamide, n-valeric amide, n-capronamide, methacrylamide, phenylacetamide, cyclohexanecarboxamide, and the like. The additive amount of the inducer to the medium is from 0.050 to 2.0%, preferably from 0.1% to 1.0%.

The cultivation can be aerobically carried out, and typically the incubation time is about from 1 to 5 days, the pH of the medium is from 3 to 9, the incubation temperature is from 10 to 50° C.

In the present invention, the stereoselective hydrolysis reaction of the racemic nipecotamide derivative (1) can be carried out by adding the racemic nipecotamide derivative (1) as a substrate and a culture of the microorganism or processed product thereof or the like into a suitable solvent, and stirring the mixture while the pH is adjusted. Although the reaction conditions vary depending on the enzyme, the microorganism or processed product thereof to be used, the substrate concentration, and the like, typically the substrate concentration can be about from 0.1 to 100% by weight, preferably from 1 to 60% by weight, the reaction temperature can be from 10 to 60° C., preferably from 20 to 50° C., the pH of the reaction can be from 4 to 11, preferably from 6 to 9, and the reaction time can be from 1 to 120 hours, preferably from 1 to 72 hours. The substrate can be collectively or continuously added. The reaction can be carried out batchwise or continuously.

The optically active nipecotamide derivative and optically active nipecotic acid derivative generated by the reaction can be each isolated and purified by the common procedure. For example, the reaction mixture including the optically active nipecotamide derivative generated by the hydrolysis reaction is treated with sodium hydroxide or the like, and extracted with an organic solvent such as ethyl acetate or toluene, and the organic solvent is evaporated under reduced pressure, and the target compound can be isolated and purified by distillation, recrystallization, chromatography or the like. Additionally, the filtrate prepared by removing the cell of the microorganism from the reaction mixture is neutralized and crystallized using sodium hydroxide or the like, and then the precipitated target compound is filtrated for isolation and purification.

The method of producing optically active 3-aminopiperidine or salt thereof from optically active nipecotamide via step 2 to step 5 is described below.

Step 2

In the present step, an optically active 1-aroylnipecotamide derivative represented by the following formula (4):

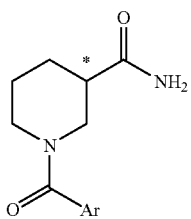

(4)

wherein, * indicates an asymmetric carbon atom; Ar represents an optionally substituted aryl group having 6 to 15 carbon atoms, is produced by aroylating optically active nipecotamide represented by the following formula (2'):

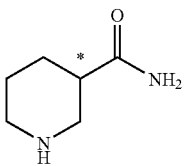

(2')

wherein, * indicates an asymmetric carbon atom.

In the present invention, an aryl group preferably includes a phenyl group, a naphthyl group and a biphenyl group, preferably a phenyl group. The substituent includes an alkyl group having 1 to 12 carbon atoms, an alkenyl group having 2 to 12 carbon atoms, an aralkyl group having 7 to 12 carbon atoms, an aryl group having 6 to 12 carbon atoms, a fluorine atom, a chlorine atom, a bromine atom, an iodine atom, an alkyloxy group having 1 to 12 carbon atoms, an alkylthio group having 1 to 12 carbon atoms, a nitro group, an amino group, a nitroso group, a hydroxyl group, a sulfonic acid group, a sulfonamide group, a carboxylic acid group, a formyl group, an acyl group having 2 to 12 carbon atoms, an aroyl group having 7 to 12 carbon atoms, a cyano group, an alkyloxycarbonyl group having 2 to 12 carbon atoms, a trifluoromethyl group, and the like. The substituent is preferably an alkyl group having 1 to 12 carbon atoms and a chlorine atom.

Ar is particularly preferably a phenyl group, a p-methylphenyl group and a p-chlorophenyl group, and the optically active 1-aroyl nipecotamide derivative (4) in which the Ar is the groups is a novel compound unknown in literatures.

The method for producing the optically active nipecotamide represented by the formula (2') that is a starting material of the present step is not particularly limited; and, for example, the optically active nipecotamide in which $R^1$ in the formula (2) produced in step 1 is a hydrogen atom may be used, and the compound produced according to the method described in JP7-133273 A and like may be used.

In the present step, the nitrogen atom of the compound (2') is aroylated by reacting an aroylating agent in the presence of a base.

The aroylating agent includes acid anhydrides such as benzoic anhydride, p-methylbenzoic anhydride and p-chlorobenzoic anhydride, and acid chlorides such as benzoyl chloride, p-toluoyl chloride and p-chlorobenzoyl chloride.

The use amount of the aroylating agent is preferably 0.5 to 10 times by mole, more preferably 1 to 5 times by mole, relative to the compound (2').

The base is not particularly limited, and the example thereof includes tertiary amines such as triethylamine, tri-n-butylamine, N-methyl morpholine, N-methylpiperidine, diisopropylethylamine, pyridine, N,N-dimethylaminopyridine and 1,4-diazabicyclo[2,2,2]octane; metal hydroxides such as lithium hydroxide, sodium hydroxide, potassium hydroxide, barium hydroxide and magnesium hydroxide; metal carbonates such as lithium carbonate, sodium carbonate and potassium carbonate; metal bicarbonate salts such as lithium hydrogen carbonate, sodium hydrogen carbonate and potassium hydrogen carbonate; and metal alkoxides such as lithium methoxide, lithium ethoxide, sodium methoxide, sodium ethoxide, potassium methoxide, potassium ethoxide and potassium-tert-butoxide.

The base is preferably lithium hydroxide, sodium hydroxide, potassium hydroxide, lithium carbonate, sodium carbonate and potassium carbonate, more preferably sodium hydroxide and potassium hydroxide.

The use amount of the base is preferably 0.1 to 10 times by mole, more preferably 1 to 5 times by mole, relative to the compound (2').

The reaction solvent of the present step includes water; alcoholic solvents such as methanol, ethanol and isopropanol; ether type solvents such as tetrahydrofuran, 1,4-dioxane and ethylene glycol dimethyl ether; ester solvents such as ethyl acetate and isopropyl acetate; hydrocarbon solvents such as benzene, toluene, xylene and hexane; ketone solvents such as acetone and methyl ethyl ketone; nitrile solvents such as acetonitrile, propionitrile and benzonitrile; halogen type solvents such as methylene chloride, chloroform and chlorobenzene; amide solvents such as N,N-dimethylformamide and N,N-dimethylacetoamide; sulfoxide solvents such as dimethyl sulfoxide; urea solvents such as dimethylpropylene urea; and triamide phosphonate solvents such as triamide hexamethylphosphonate. One of the solvents may be singly used, or two or more solvents may be used in combination. Water is preferred.

The use amount of the solvent is preferably 50 times or less by weight, more preferably 20 times or less by weight, relative to the compound (2').

When the present reaction is carried out in a water-containing solvent, hydrolysis of the aroylating agent proceeds. Thus, in such a case, it is preferable that the reaction may be carried out while the pH of the reaction mixture is adjusted, and the aroylating agent and the base are gradually added. The pH of the reaction mixture is preferably from 6 to 14, more preferably from 7 to 11.

The reaction temperature of the present step is preferably from −20 to 80° C., more preferably from 0 to 50° C. Although the reaction time of the step is not particularly limited, the time is preferably from 30 minutes to 24 hours, more preferably from 1 to 6 hours.

Though the addition method and addition order of the compound (2'), the base, the aroylating agent and the reaction solvent upon the reaction are not particularly limited, as described previously, the base and the aroylating agent are preferably gradually added to a mixture of the compound (2') and the reaction solvent while the pH is adjusted.

The reaction mixture obtained in the present step may also be used directly in the subsequent step, and if necessary, may also be post-processed. General treatment for obtaining a product from a reaction mixture may be carried out as post-processing. For example, water or, as necessary, an aqueous acid solution such as an hydrochloric acid or diluted sulfuric acid is added to the reaction mixture after completion of the reaction for neutralization; and extraction may be carried out using a general extraction solvent such as ethyl acetate, diethyl ether, methylene chloride, toluene, hexane. The reaction solvent and extraction solvent are evaporated from the thus obtained extract by an operation such as heating under reduced pressure to obtain the target compound.

Although the thus obtained target compound has a purity enough to be usable in the following step, the purity may also be further improved by a general purification measure such as crystallization, fractional distillation or column chromatography for the purpose of further improving the yield in the following step or the purity of a compound obtained in the following step.

Alternatively, when the compound (4) that is a product is already precipitated in the reaction mixture as crystal, the crystal may be simply separated. As the method of separating the crystal, pressure filtration, vacuum filtration and centrifugal separation may also be all acceptable. The crystal may also be washed with water or an organic solvent in order to further improve the purity of the crystal.

The organic solvent includes alcoholic solvents such as methanol, ethanol and isopropanol; ether type solvents such as tetrahydrofuran, 1,4-dioxane and ethylene glycol dimethyl ether; ester solvents such as ethyl acetate and isopropyl acetate; hydrocarbon solvents such as benzene, toluene, xylene and hexane; ketone solvents such as acetone and methyl ethyl ketone; nitrile solvents such as acetonitrile, propionitrile and benzonitrile; halogen type solvents such as methylene chloride, chloroform and chlorobenzene. One of the solvents may be singly used, or two or more solvents may be used in combination. The organic solvent is preferably ethyl acetate, toluene, xylene, hexane and chlorobenzene.

Step 3

In the present step, an optically active 1-aroyl-3-aminopiperidine derivative represented by the following formula (5):

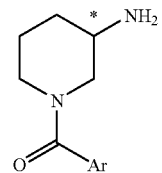

wherein, * and Ar mean the same as the above, is produced by Hofmann rearrangement at the amide group of the optically active 1-aroylnipecotamide derivative which is produced in Step 2 and represented by the following formula (4):

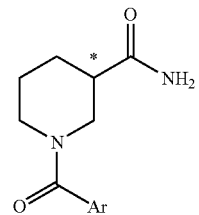

wherein, * and Ar mean the same as the above.

Particularly, the optically active 1-aroyl-3-aminopiperidine derivative (5) in which Ar is a phenyl group, a p-methylphenyl group or a p-chlorophenyl group is a novel compound unknown in literatures.

The Hofmann rearrangement can be carried out by reacting the compound (4) with an oxidizing agent and a base.

The oxidizing agent includes, for example, chlorine, bromine and sodium hypochlorite, preferably sodium hypochlorite. When sodium hypochlorite is used, aqueous solution thereof may be used from the viewpoints of storage stability and easiness of handling. The concentration of the aqueous solution is preferably from 5 to 30% by weight.

The use amount of the oxidizing agent is preferably 1 to 10 times by mole, more preferably 1 to 3 times by mole, relative to the compound (4).

The base includes, for example, metal hydroxides such as lithium hydroxide, sodium hydroxide, potassium hydroxide, barium hydroxide and magnesium hydroxide; metal alkoxides such as lithium methoxide, lithium ethoxide, sodium methoxide, sodium ethoxide, potassium methoxide, potassium ethoxide and potassium tert-butoxide. The base is preferably lithium hydroxide, sodium hydroxide and potassium hydroxide.

The use amount of the base is preferably 0.5 to 30 times by mole, more preferably 3 to 15 times by mole, relative to the compound (4).

The reaction temperature of the present step is preferably from −20 to 100° C., more preferably from −5 to 70° C. The reaction time of the step is preferably from 30 minutes to 24 hours, more preferably from 1 to 12 hours.

The reaction solvent of the step is not particularly limited, and water and a general organic solvent can be used. Among them, water is preferred. The usable organic solvent includes alcoholic solvents such as methanol, ethanol and isopropanol; ether type solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen type solvents such as methylene chloride and chloroform; amide solvents such as N,N-dimethylformamide and N,N-dimethylacetoamide; sulfoxide solvents such as dimethyl sulfoxide; urea solvents such as dimethylpropylene urea; and triamide phosphonate solvents such as triamide hexamethylphosphonate. One of the solvents may be singly used, or two or more solvents may be used in combination. When two or more solvents are used, the mixing ratio is not particularly limited.

The use amount of the solvent is preferably 50 times or less by weight, more preferably 20 times or less by weight, relative to the compound (4).

The addition method and addition order of the compound (4), the oxidizing agent, the base and the reaction solvent upon the reaction are not particularly limited, and the oxidizing agent may be added dropwise lastly from the viewpoint of improving the yield.

As for the processing after the reaction, extraction using ethyl acetate, toluene and isopropyl ether, which are representative extraction solvents, is difficult, since the compound (5) obtained in the present step typically exhibits high water solubility. On the other hand, the compound (5) can be extracted if a large amount of an organic solvent having a large polarity, such as tetrahydrofuran or isopropanol, is used. However, in such a case, inorganic salt and organic impurity are also extracted together, whereby it is difficult to obtain the compound (5) with high purity. The present inventors intensely studied the problem; as a result, found that the compound is converted into a water-insoluble compound by carrying out step 4 described below, and it becomes easy to isolate the compound.

Step 4

In the present step, the amino group of the optically active 1-aroyl-3-aminopiperidine derivative which is produced in Step 3 and represented by the following formula (5):

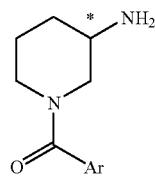

(5)

wherein, * and Ar mean the same as the above, is aroylated or carbamated to produce an optically active 1-aroyl-3-(protected amino)piperidine derivative represented by the following formula (6):

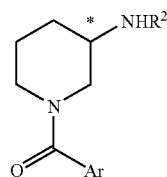

(6)

wherein, * and Ar mean the same as the above; $R^2$ represents an optionally substituted aroyl group having 7 to 15 carbon atoms, an alkyloxycarbonyl group having 2 to 15 carbon atoms, an alkenyloxycarbonyl group having 3 to 15 carbon atoms, an aryloxycarbonyl group having 7 to 15 carbon atoms, or an aralkyloxycarbonyl group having 8 to 15 carbon atoms. Then, the compound (6) having improved purity is isolated with crystallization using water or extraction with an organic solvent.

$R^2$ is preferably a benzoyl group, an o-methylbenzoyl group, a m-methylbenzoyl group, a p-methylbenzoyl group, an o-chlorobenzoyl group, a m-chlorobenzoyl group, a p-chlorobenzoyl group, a p-methoxybenzoyl, a p-nitrobenzoyl group, a 3,4-dichlorobenzoyl group, a tert-butoxycarbonyl group, a methoxycarbonyl group, an ethoxycarbonyl group, an n-propoxycarbonyl group, an isopropoxycarbonyl group, an n-butoxycarbonyl group, an isobutoxycarbonyl group, an allyloxycarbonyl group and phenyloxycarbonyl group, more preferably a benzoyl group, a p-methylbenzoyl group, a p-chlorobenzoyl group and a tert-butoxycarbonyl group. The optically active 1-aroyl-3-(protected amino)piperidine derivative (6) in which $R^2$ represents the above groups is a novel compound unknown in literatures.

The aroylation or carbamation of the present step is carried out by reacting an aroylating agent or a carbamating agent in the presence of a base.

The aroylating agent includes acid anhydrides such as benzoic anhydride, p-methylbenzoic anhydride and p-chlorobenzoic anhydride, and acid chlorides such as benzoyl chloride, p-methylbenzoyl chloride and p-chlorobenzoyl chloride. The agent is preferably acid chlorides such as benzoyl chloride, p-methylbenzoyl chloride and p-chlorobenzoyl chloride.

The carbamating agent includes di-tert-butyl dicarbonate, dibenzyl dicarbonate, methyl chlorocarbonate, ethyl chlorocarbonate, n-propyl chlorocarbonate, isopropyl chlorocarbonate, n-butyl chlorocarbonate, isobutyl chlorocarbonate, allyl chlorocarbonate, phenyl chlorocarbonate and benzyl chlorocarbonate, preferably di-tert-butyl dicarbonate and benzyl chlorocarbonate.

The use amount of the aroylating agent or carbamating agent is preferably 0.5 to 10 times by mole, more preferably 1 to 5 times by mole, relative to the compound (5).

The base is not particularly limited, and the example thereof includes tertiary amines such as triethylamine, tri-n-butylamine, N-methyl morpholine, N-methylpiperidine, diisopropylethylamine, pyridine, N,N-dimethylaminopyridine and 1,4-diazabicyclo[2,2,2]octane; metal hydroxides such as lithium hydroxide, sodium hydroxide, potassium hydroxide, barium hydroxide and magnesium hydroxide; metal carbonates such as lithium carbonate, sodium carbonate and potassium carbonate; metal bicarbonate salts such as lithium hydrogen carbonate, sodium hydrogen carbonate and potassium hydrogen carbonate; and metal alkoxides such as lithium methoxide, lithium ethoxide, sodium methoxide, sodium ethoxide, potassium methoxide, potassium ethoxide and potassium-tert-butoxide. The base is preferably lithium hydroxide, sodium hydroxide, potassium hydroxide, lithium carbonate, sodium carbonate and potassium carbonate, more preferably sodium hydroxide and potassium hydroxide.

The use amount of the base is preferably 0.1 to 10 times by mole, more preferably 1 to 5 times by mole, relative to the amount of the compound (5).

The reaction solvent of the present step is a solvent used in step 3, and is preferably water. An organic solvent may be further added, as required, for the purpose of improving at least one of the promotion of the reaction, yield improvement, improvement of liquid properties, and the like.

The hydrolysis of the aroylating agent or carbamating agent proceeds when water is contained in the reaction solvent of the step. Thus, in such a case, the reaction may be carried out while the pH of the reaction mixture is adjusted and the aroylating agent or carbamating agent and the base are gradually added.

The pH of the reaction mixture is preferably from 6 to 14, more preferably from 7 to 11.

The reaction temperature of the present step is preferably from −20 to 80° C., more preferably from 0 to 50° C.

Although the reaction time of the step is not particularly limited, the time is preferably from 30 minutes to 24 hours, more preferably from 1 to 6 hours.

Though the method and order of addition of the compound (5), the base, the aroylating agent or carbamating agent and the reaction solvent upon the reaction are not particularly limited, as described previously, the base and the aroylating agent or carbamating agent are preferably gradually added to the mixture of the compound (5) and the reaction solvent while the pH is adjusted.

When the compound (6) that is the product is already precipitated as crystal in the reaction mixture, the crystal may directly be separated as the treatment after the reaction. As the method for separating the crystal, pressure filtration, vacuum filtration and centrifugal separation may also be all acceptable. The crystal may also be washed with water or an organic solvent in order to further improve the purity of the crystal.

The organic solvent includes alcoholic solvents such as methanol, ethanol and isopropanol; ether type solvents such as tetrahydrofuran, 1,4-dioxane and ethylene glycol dimethyl ether; ester solvents such as ethyl acetate and isopropyl acetate; hydrocarbon solvents such as benzene, toluene, xylene and hexane; ketone solvents such as acetone and methyl ethyl ketone; nitrile solvents such as acetonitrile, propionitrile and benzonitrile; halogen type solvents such as methylene chloride, chloroform and chlorobenzene. One of the solvents may be singly used, or two or more solvents may be used in combination. The organic solvent is preferably ethyl acetate, toluene, xylene, hexane and chlorobenzene.

Alternatively, the compound (6) that is the product may also be extracted with an organic solvent for isolation as another method.

The organic solvent is not particularly limited so long as the solvent is difficult to be mixed with water, and preferably includes ether type solvents such as tetrahydrofuran, 1,4-dioxane and ethylene glycol dimethyl ether; ester solvents such as ethyl acetate and isopropyl acetate; hydrocarbon solvents such as benzene, toluene, xylene and hexane; halogen type solvents such as methylene chloride, chloroform and chlorobenzene; more preferably ethyl acetate, toluene, xylene, chlorobenzene, and the like.

The use amount of the organic solvent is preferably 50 times or less by weight, more preferably 20 times or less by weight, relative to the compound (6).

It is preferable to carry out extraction at room temperature or higher, preferably at 50 to 130° C., in order to improve the solubility of the compound (6) in the organic solvent to thereby reduce the use amount of the solvent.

The product through steps 1 to 4 contains an optically active 1-aroylnipecotic acid as impurity, represented by the following formula (11):

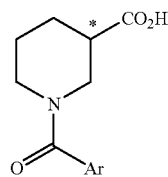

(11)

wherein, * and Ar mean the same as the above,

In order to remove the compound, the pH of the water layer may be preferably adjusted to be 7 or higher, more preferably from 9 to 14.

The purity of the compound (6) separated with extraction can be improved by evaporating the solvent by the operation such as heating under reduced pressure. When the compound (6) has good crystallinity, the compound may be crystallized and purified to obtain the compound (6) with high quality. The impurity to be removed includes the compound (11), the enantiomer of the compound (6), the excessive aroylating agent or carbamating agent, and the like. The method for crystallizing the compound (6) may be any crystallization methods such as crystallization by cooling an extract, crystallization by concentrating under reduced pressure and crystallization by adding a poor solvent such as hexane and heptane.

Step 5

In the present step, optically active 3-aminopiperidine or salt thereof represented by the following formula (7):

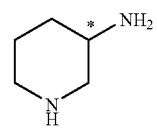

(7)

wherein, * indicates an asymmetric carbon atom, is produced by hydrolyzing the optically active 1-aroyl-3-(protectedamino)piperidine derivative which is produced in Step 4 and is represented by the following formula (6):

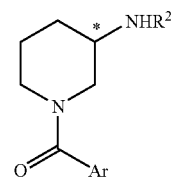

(6)

wherein, *, Ar and $R^2$ mean the same as the above.

In the present step, compound (6) is reacted with an acid or a base for hydrolysis. Preferably, an acid may be used.

The base is not particularly limited, and the example thereof includes sodium hydroxide, potassium hydroxide and lithium hydroxide.

The use amount of the base is preferably 20 times or less by mole, more preferably 1 to 10 times by mole, relative to the amount of the compound (6).

The acid is not particularly limited, and the example thereof includes mineral acids such as hydrogen chloride, hydrogen bromide, sulfuric acid and nitric acid; and sulfonic acids such as trifluoromethane sulfonic acid, p-toluenesulfonic acid and methanesulfonic acid. The acid is preferably hydrogen chloride, hydrobromic acid and sulfuric acid, more preferably hydrogen chloride. Although the acid may be used directly, the aqueous solution thereof is preferably used.

The use amount of the acid is preferably 50 times or less by mole, more preferably 1 to 20 times by mole, relative to the compound (6).

The reaction temperature of the present step is preferably from 30° C. to 200° C., more preferably from 50° C. to 140° C.

Although the reaction time of the step is not particularly limited, the time is preferably from 1 to 40 hours, more preferably from 5 to 30 hours.

The reaction solvent of the step is water, and an organic solvent may be further added for the purpose of the promotion of the reaction, the improvement of the liquid properties, and the like.

The organic solvent includes alcoholic solvents such as methanol, ethanol and isopropanol; and ether type solvents such as tetrahydrofuran, 1,4-dioxane and ethylene glycol dimethyl ether. One of the solvents may be singly used, or two or more solvents may be used in combination. When two or more solvents are used in combination, the mixing ratio is not particularly limited.

The addition method and addition order of the compound (6), the acid and the reaction solvent upon the reaction are not particularly limited.

General treatment for obtaining a product from a reaction mixture may be carried out as the treatment after the reaction. For example, as necessary, an aqueous alkaline solution such as an aqueous sodium hydroxide solution or aqueous potassium carbonate solution is added to the reaction mixture after completion of the reaction for neutralization, and extraction may be carried out using a general extraction solvent such as ethyl acetate, diethyl ether, methylene chloride, toluene, hexane or the like. The reaction solvent and extraction solvent are evaporated from the resulting extract by an operation such as heating under reduced pressure to obtain the target compound.

Although the thus obtained target compound has purity enough to be usable in the following step, the purity may also be further improved by a general purifying method such as crystallization, fractional distillation or column chromatography for the purpose of further improving the yield in the following step or the purity of a compound obtained in the following step.

Alternatively, the reaction solvent may be evaporated from the reaction mixture by an operation such as heating under reduced pressure to isolate the target compound as a salt of the compound (7) and the acid, and crystallization may be carried out for the purpose of further improving the purity.

The solvent for carrying out crystallization preferably includes alcoholic solvents such as methanol, ethanol and isopropanol; ether type solvents such as tetrahydrofuran, 1,4-dioxane and ethylene glycol dimethyl ether; ester solvents such as ethyl acetate and isopropyl acetate; hydrocarbon solvents such as benzene, toluene, xylene and hexane; and halogen type solvents such as methylene chloride, chloroform and chlorobenzene. One of the solvents may be singly used, or two or more solvents may be used in combination. The solvent is more preferably methanol, ethanol, ethyl acetate, toluene, xylene, chlorobenzene and the like.

Moreover, optically active 3-aminopiperidine or salt thereof can be obtained also by the following scheme. Each step is described below in order.

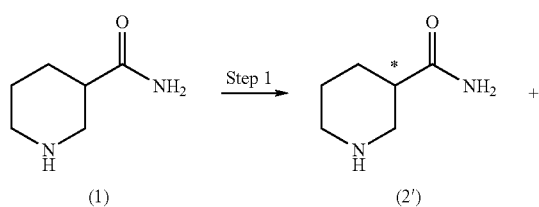

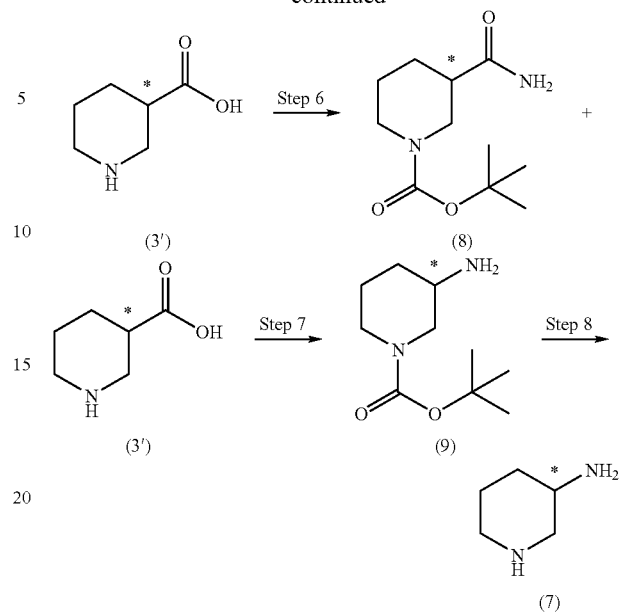

Step 6

In the present step, only optically active nipecotamide which is produced in Step 1 and is represented by the following formula (2'):

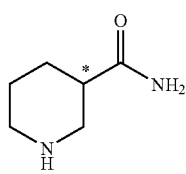

wherein, * indicates an asymmetric carbon atom, is selectively protected with a tert-butoxycarbonyl group, in a mixture of the compound (2') and optically active nipecotic acid represented by the following formula (3'):

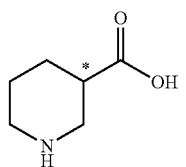

wherein, * means the same as the above, to obtain optically active 1-(tert-butoxycarbonyl)nipecotamide represented by the following formula (8):

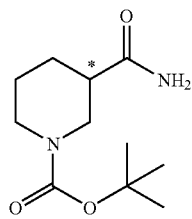

wherein, * means the same as the above, and the compound (8) is separated from the compound (3').

When the protection with a t-butoxycarbony group is carried out by a conventional method, the optically active nipecotic acid represented by the formula (3') is also protected with a t-butoxycarbony group; as a result, an expensive butoxycarbonylating agent is wasted. Therefore, the present inventors found that only the compound (2') could be highly selectively t-butoxycarbonylated by adjusting the pH in bilayer of an organic solvent and water.

Di-tert-butyl dicarbonate is preferred as the butoxycarbonylating agent. The use amount of the butoxycarbonylating agent is preferably 0.5 to 5 equivalents, more preferably 0.8 to 2 equivalents, relative to the compound (2').

In the present step, the pH is adjusted by further adding a base.

The base includes metal hydroxides such as lithium hydroxide, sodium hydroxide, potassium hydroxide, barium hydroxide and magnesium hydroxide; metal carbonates such as lithium carbonate, sodium carbonate and potassium carbonates; metal hydrogen carbonate salts such as lithium hydrogen carbonate, sodium hydrogen carbonate and potassium hydrogen carbonate; and metal alkoxides such as lithium methoxide, lithium ethoxide, sodium methoxide, sodium ethoxide, potassium methoxide, potassium ethoxide and potassium tert-butoxide. The base is preferably lithium hydroxide, sodium hydroxide, potassium hydroxide, lithium carbonate, sodium carbonate and potassium carbonate, more preferably sodium hydroxide and potassium hydroxide.

The use amount of the base is preferably 0.1 to 10 times by mole, more preferably 0.3 to 5 times by mole, relative to the compound (2').

The reaction of the present step is carried out by mixing an organic solvent with the aqueous solution containing the mixture of the compounds (2') and (3').

The organic solvent includes alcoholic solvents such as methanol, ethanol and isopropanol; ether type solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile, propionitrile and benzonitrile; halogen type solvents such as methylene chloride and chloroform; amide solvents such as N,N-dimethylformamide and N,N-dimethylacetoamide; sulfoxide solvents such as dimethyl sulfoxide; urea solvents such as dimethylpropylene urea; and triamide phosphonate solvents such as triamide hexamethylphosphonate. One of the solvents may be singly used, or two or more solvents may be used in combination.

The organic solvent is preferably tetrahydrofuran, 1,4-dioxane and isopropanol, more preferably tetrahydrofuran. If the aqueous solution containing the mixture of the compounds (2') and compound (3') and the organic solvent are not separated into two layers, an inorganic salt such as sodium chloride, lithium chloride or sodium sulfate may be further added for layer separation.

The use amount of the organic solvent is preferably 50 times or less by weight, more preferably 20 times or less by weight, relative to the compound (2').

The reaction temperature of the present step is preferably from −20 to 80° C., more preferably from 0 to 50° C. Although the reaction time of the step is not particularly limited, the time is preferably from 30 minutes to 24 hours, more preferably from 1 to 6 hours.

Though the addition method and addition order of the compound (2'), the base, the butoxycarbonylating agent and the reaction solvent upon the reaction are not particularly limited, the butoxycarbonylating agent and the base may be preferably added at the same time to the solution of the compound (2') for the purpose of adjusting the pH.

The treatment after the reaction involves adding a general extraction solvent such as ethyl acetate, diethyl ether, methylene chloride, toluene or hexane to the reaction mixture for extraction operation. In such a case, although the compound (3') is hardly extracted to the organic layer due to high water solubility, the pH of the water layer is adjusted to preferably 7 or higher, more preferably from 8 to 13 to be able to completely separate the compound (3') into the organic layer. The reaction solvent and extraction solvent are evaporated from the resulting extract by an operation such as heating under reduced pressure to obtain the target compound. Alternatively, the organic solvent is evaporated under reduced pressure from the solution after the reaction, or a poor solvent such as hexane or methylcyclohexane is added to thereby be capable of precipitating the target compound as crystal. The crystal may be filtered off and isolated by pressure filtration, vacuum filtration or centrifugal separation.

Although the target compound obtained by the method has a purity enough to be usable in the following step, the purity may also be further improved by a general purifying means such as crystallization, fractional distillation or column chromatography for the purpose of further improving the yield in the following step or the purity of a compound obtained in the following step.

Step 7

In the present step, optically active 1-(tert-butoxycarbonyl)-3-aminopiperidine or salt thereof, represented by the following formula (9):

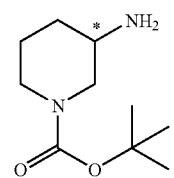

(9)

wherein, * means the same as the above,
is produced by Hofmann rearrangement at the amide group of the optically active 1-(tert-butoxycarbonyl)nipecotamide which is produced in Step 6 and is represented by the following formula (8):

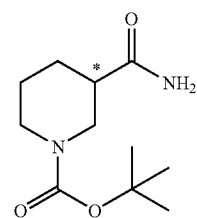

(8)

wherein, * means the same as the above.

In the present step, the compound (8) is reacted with an oxidizing agent and a base to carry out Hofmann rearrangement.

The oxidizing agent includes, for example, chlorine, bromine and sodium hypochlorite. The oxidizing agent is preferably sodium hypochlorite, and aqueous sodium hypochlorite solution may be preferably used from the viewpoints of storage stability and easiness of handling. The concentration of the aqueous solution is preferably from 5 to 30% by weight. The use amount of the oxidizing agent is preferably 1 to 10 times by mole, more preferably 1 to 3 times by mole, relative to the compound (8).

The base includes, for example, metal hydroxides such as lithium hydroxide, sodium hydroxide, potassium hydroxide, barium hydroxide and magnesium hydroxide; metal alkoxides such as lithium methoxide, lithium ethoxide, sodium methoxide, sodium ethoxide, potassium methoxide, potassium ethoxide and potassium tert-butoxide. The base is preferably lithium hydroxide, sodium hydroxide and potassium hydroxide.

The use amount of the base is preferably 0.5 to 30 times by mole, more preferably 3 to 15 times by mole, relative to the compound (8).

The reaction temperature of the present step is preferably from −20 to 100° C., more preferably from −5 to 70° C.

The reaction time of the step is preferably from 30 minutes to 24 hours, more preferably from 1 to 12 hours.

Water is preferred as the reaction solvent of the step. In addition, an organic solvent may be further coexisted in order to promote the reaction.

The use amount of the solvent is preferably 50 times or less by weight, more preferably 20 times or less by weight, relative to the compound (8).

The addition method and addition order of the compound (8), the oxidizing agent, the base and the reaction solvent upon the reaction are not particularly limited; however, the oxidizing agent may be added dropwise lastly from the viewpoint of improving the yield.

General treatment for obtaining a product from a reaction mixture may be carried out as the treatment after the reaction. For example, water or, as necessary, an aqueous acid solution such as hydrochloric acid or diluted sulfuric acid is added to the reaction mixture after completion of the reaction for neutralization, and extraction may be carried out using a general extraction solvent such as ethyl acetate, diethyl ether, methylene chloride, toluene, hexane or the like. The reaction solvent and extraction solvent are evaporated from the resulting extract by an operation such as heating under reduced pressure to obtain the target compound. Although the thus obtained target compound has purity enough to be usable in the following step, the purity may also be further improved by a general purifying means such as crystallization, fractional distillation or column chromatography for the purpose of further improving the yield in the following step or the purity of a compound obtained in the following step.

Step 8

In the present step, optically active 3-aminopiperidine or salt thereof, represented by the following formula (7):

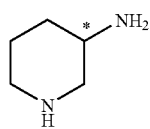

(7)

wherein, * indicates an asymmetric carbon atom, is produced by treating optically active 1-(tert-butoxycarbonyl)-3-aminopiperidine or salt thereof which is produced in Step 7 and is represented by the following formula (9)

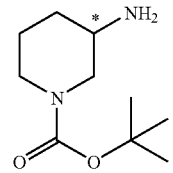

(9)

wherein, * means the same as the above, with an acid for deprotection at 1-position.

The acid is not particularly limited, and the example thereof includes mineral acids such as hydrogen chloride, hydrogen bromide, sulfuric acid and nitric acid, and sulfonic acids such as trifluoromethane sulfonic acid, p-toluenesulfonic acid and methanesulfonic acid. The acid is preferably hydrogen chloride, hydrobromic acid and sulfuric acid, more preferably hydrogen chloride. Although the acid may be used directly, the solution prepared by dissolving the acid in methanol, ethanol, isopropanol, 1,4-dioxane or water is rather preferred.

The use amount of the acid is preferably 50 times or less by mole, more preferably 1 to 20 times by mole, relative to the compound (9). The reaction temperature of the present step is preferably from 30 to 200° C., more preferably from 50° C. to 140° C. Although the reaction time of the reaction is not particularly limited, the time is preferably from 1 to 40 hours, more preferably from 5 to 30 hours.

The reaction solvent includes water; alcoholic solvents such as methanol, ethanol and isopropanol; and ether type solvents such as tetrahydrofuran, 1,4-dioxane and ethylene glycol dimethyl ether. One of the solvents may be singly used, or two or more solvents may be used in combination. When two or more solvents are used in combination, the mixing ratio is not particularly limited. The reaction solvent is alcoholic solvents such as methanol, ethanol and isopropanol.

The addition method and addition order of the compound (9), the acid and the reaction solvent upon the reaction are not particularly limited.

General treatment for obtaining a product from a reaction mixture may be carried out as the treatment after the reaction. For example, water or, as necessary, an aqueous alkaline solution such as an aqueous sodium hydroxide solution or aqueous potassium carbonate solution is added to the reaction mixture after completion of the reaction for neutralization, and extraction may be carried out using a general extraction solvent such as ethyl acetate, diethyl ether, methylene chloride, toluene, hexane or the like. The reaction solvent and extraction solvent are evaporated from the resulting extract by an operation such as heating under reduced pressure to obtain the target compound.

Although thus obtained target compound has purity enough to be usable in the following step, the purity may also be further improved by a general purifying means such as crystallization, fractional distillation or column chromatography for the purpose of further improving the yield in the following step or the purity of a compound obtained in the following step.

Alternatively, the reaction solvent may be evaporated from the reaction mixture by an operation such as heating under reduced pressure to isolate the target compound as a salt of the compound (7) and the acid or to crystallize the target compound for the purpose of further improving the purity.

The solvent for carrying out crystallization preferably includes alcoholic solvents such as methanol, ethanol and isopropanol; ether type solvents such as tetrahydrofuran, 1,4- dioxane and ethylene glycol dimethyl ether; ester solvents such as ethyl acetate and isopropyl acetate; hydrocarbon solvents such as benzene, toluene, xylene and hexane; and halogen type solvents such as methylene chloride, chloroform and chlorobenzene. One of the solvents may be singly used, or two or more solvents may be used in combination. The solvent is more preferably methanol, ethanol, ethyl acetate, toluene, xylene, chlorobenzene and the like.

Moreover, optically active 3-aminopiperidine or salt thereof can be obtained also by the following scheme. Each step is sequentially described below.

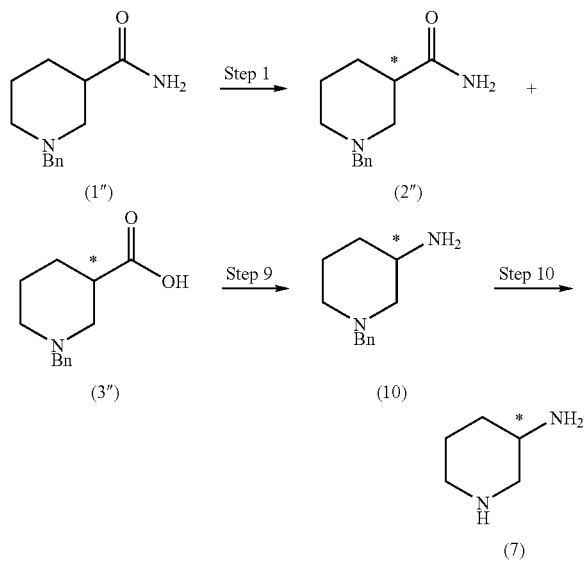

Step 9

In the present step, optically active 1-(benzyl)amino piperidine or salt thereof represented by the following formula (10):

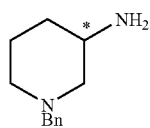

wherein, * indicates an asymmetric carbon atom, is produced by Hofmann rearrangement at the amide group of the optically active 1-(benzyl)nipecotamide which is produced in Step 1 and represented by the following formula (2"):

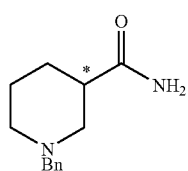

wherein, * means the same as the above.

In the present step, the compound (2") is reacted with an oxidizing agent and a base to carry out the Hofmann rearrangement.

The oxidizing agent includes, for example, chlorine, bromine and sodium hypochlorite. The oxidizing agent is preferably sodium hypochlorite, and the aqueous solution thereof may be used from the viewpoints of storage stability and easiness of handling. The concentration of the aqueous solution is preferably from 5 to 30% by weight.

The use amount of the oxidizing agent is preferably 1 to 10 times by mole, more preferably 1 to 3 times by mole, relative to the compound (2").

The base includes, for example, metal hydroxides such as lithium hydroxide, sodium hydroxide, potassium hydroxide, barium hydroxide and magnesium hydroxide; metal alkoxides such as lithium methoxide, lithium ethoxide, sodium methoxide, sodium ethoxide, potassium methoxide, potassium ethoxide and potassium tert-butoxide. The base is preferably lithium hydroxide, sodium hydroxide and potassium hydroxide.

The use amount of the base is preferably 0.5 to 30 times by mole, more preferably 3 to 15 times by mole, relative to the compound (2"). The reaction temperature of the present step is preferably from −20 to 100° C., more preferably from −5 to 70° C.

The reaction time of the step is preferably from 30 minutes to 24 hours, more preferably from 1 to 12 hours.

The reaction solvent of the step is not particularly limited, and water and a general organic solvent can be used. Among them, water is preferred. The organic solvent to be used includes alcoholic solvents such as methanol, ethanol and isopropanol; ether type solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen type solvents such as methylene chloride and chloroform; amide solvents such as N,N-dimethylformamide and N,N-dimethylacetoamide; sulfoxide solvents such as dimethyl sulfoxide; urea solvents such as dimethylpropylene urea; and triamide phosphonate solvents such as triamide hexamethylphosphonate. One of the solvents may be singly used, or two or more solvents may be used in combination. When two or more solvents are used in combination, the mixing ratio is not particularly limited.

The use amount of the solvent is preferably 50 times or less by weight, more preferably 20 times or less by weight, relative to the compound (2").

The addition method and addition order of the compound (2"), the oxidizing agent, the base and the reaction solvent upon the reaction are not particularly limited, and the oxidizing agent may be added dropwise lastly from the viewpoint of improving the yield.

General treatment for obtaining a product from a reaction mixture may be carried out as the treatment after the reaction. For example, water or, as necessary, an aqueous acid solution such as hydrochloric acid solution or diluted sulfuric acid is added to the reaction mixture after completion of the reaction for neutralization, and extraction may be carried out using a general extraction solvent such as ethyl acetate, diethyl ether, methylene chloride, toluene, hexane or the like. The reaction solvent and extraction solvent are evaporated from the resulting extract by an operation such as heating under reduced pressure to obtain a target substance.

Although the thus obtained target compound has purity enough to be usable in the following step, the purity may also be further improved by a general purifying means such as crystallization, fractional distillation or column chromatography for the purpose of further improving the yield in the following step or the purity of a compound obtained in the following step.

Step 10

In the present step, optically active 3-aminopiperidine or salt thereof represented by the following formula (7):

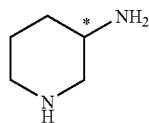
(7)

wherein, * indicates an asymmetric carbon atom,
is produced by reacting the optically active 1-(benzyl)amino piperidine or salt thereof which is produced in Step 9 and represented by the following formula (10):

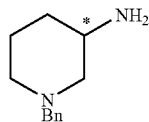
(10)

wherein, * means the same as the above,
with a hydrogen source in the presence of a catalyst for deprotection at 1-position by additional hydrogen decomposition.

The hydrogen source is not particularly limited, and the example thereof includes hydrogen, formic acid and ammonium formate, preferably hydrogen.

The catalyst is not particularly limited, and the example thereof includes palladium, palladium hydroxide, platinum, rhodium and ruthenium. The catalyst is preferably palladium and palladium hydroxide. The catalyst may be directly used, or a supported catalyst on activated charcoal, silica gel, alumina or the like may also be used.

In the present reaction, an acid may be added for the implementation of the reaction.

The acid is not particularly limited, and the example thereof includes mineral acids such as hydrogen chloride, hydrogen bromide, sulfuric acid and nitric acid; sulfonic acids such as trifluoromethane sulfonic acid, p-toluenesulfonic acid and methanesulfonic acid; and carboxylic acids such as acetate, propionic acid and butyric acid. The acid is preferably hydrogen chloride, hydrobromic acid and sulfuric acid, more preferably hydrogen chloride. Although the acid may be used directly, the aqueous solution thereof is preferably used.

The use amount of the acid is preferably 50 times or less by mole, more preferably 1 to 20 times by mole, relative to the compound (10).

The reaction temperature of the present step is preferably from 0° C. to 150° C., more preferably from 10° C. to 100° C.

Although the reaction time of the reaction is not particularly limited, the time is preferably from 1 to 40 hours, more preferably from 5 to 30 hours.

The solvent of the present reaction includes water; alcoholic solvents such as methanol, ethanol and isopropanol; ether type solvents such as tetrahydrofuran, 1,4-dioxane and ethylene glycol dimethyl ether; ester solvents such as ethyl acetate and isopropyl acetate; hydrocarbon solvents such as benzene, toluene, xylene and hexane; ketone solvents such as acetone and methyl ethyl ketone; nitrile solvents such as acetonitrile, propionitrile and benzonitrile; halogen type solvents such as methylene chloride, chloroform and chlorobenzene; amide solvents such as N,N-dimethylformamide and N,N-dimethylacetoamide; sulfoxide solvents such as dimethyl sulfoxide; urea solvents such as dimethylpropylene urea; and triamide phosphonate solvents such as triamide hexamethylphosphonate. One of the solvents may be singly used, or two or more solvents may be used in combination. The solvent is preferably water; alcoholic solvents such as methanol and isopropanol.

The addition method and addition order of the compound (10), the catalyst, the hydrogen source and the reaction solvent upon the reaction are not particularly limited.

General treatment for obtaining a product from a reaction mixture may be carried out as the treatment after the reaction. For example, water or, as necessary, an aqueous alkaline solution such as an aqueous sodium hydroxide solution or aqueous potassium carbonate solution is added to the reaction mixture after completion of the reaction for neutralization, and extraction may be carried out using a general extraction solvent such as ethyl acetate, diethyl ether, methylene chloride, toluene, hexane or the like. The reaction solvent and extraction solvent are evaporated from the resulting extract by an operation such as heating under reduced pressure to obtain the target compound.

Although the thus obtained target compound has purity enough to be usable in the following step, the purity may also be further improved by a general purifying means such as crystallization, fractional distillation or column chromatography for the purpose of further improving the yield in the following step or the purity of a compound obtained in the following step.

Alternatively, the reaction solvent may be evaporated from the reaction mixture by an operation such as heating under reduced pressure to isolate the target compound as a salt of the compound (7) and the acid or to further crystallize the compound for the purpose of improving the purity.

The solvent for carrying out crystallization preferably includes alcoholic solvents such as methanol, ethanol and isopropanol; ether type solvents such as tetrahydrofuran, 1,4-dioxane and ethylene glycol dimethyl ether; ester solvents such as ethyl acetate and isopropyl acetate; hydrocarbon solvents such as benzene, toluene, xylene and hexane; and halogen type solvents such as methylene chloride, chloroform and chlorobenzene. One of the solvents may be singly used, or two or more solvents may be used in combination. The solvent is more preferably methanol, ethanol, ethyl acetate, toluene, xylene, chlorobenzene and the like.

EXAMPLES

The present invention is described in more detail by the following examples; however, the invention is by no means limited to the examples.

Example 1

Selective hydrolysis of (R)- or (S)-1-nipecotamide in racemate

Each microorganism shown in Tables 1 and 2 was inoculated in a medium (8 ml, glycerol 1.0%, peptone 0.5%, malt extract 0.3%, yeast extract 0.3%, isovaleronitrile 0.1%, pH 7.0) sterilized in vitro, and stirred and cultivated at 30° C. for 72 hours. After completion of the cultivation, the bacterial cells were collected by centrifugal separation, and suspended in 100 mM phosphate buffer (1 ml, pH 7.0). The bacterial cell suspension (0.1 ml) was mixed with 100 mM phosphate buffer containing 0.2% of racemic 1-benzylnipecotamide (0.1 ml, pH 7.0), and the mixture was shaken at 30° C. for 24 hours. After completion of the reaction, solid substance was removed by centrifugal separation, and then the substrate and product in the reaction mixture were analyzed by high performance liquid chromatography to determine the conversion rate (%) and optical purity (% ee). The results are shown in Tables 1 and 2. The KNK-J915 strain is deposited under the accession number FERM BP-10739 with International Patent Organism Depositary, National Institute of Advanced Industrial Science and Technology (Zip Code 305-8566 Chuou No. 6, 1-1-1 Higashi Tsukuba City Ibaraki Prefecture).

Conversion rate (%)=amount of product/(amount of substrate+amount of product)×100

Optical purity (% ee)=(A−B)/(A+B)×100 (A and B represent the amount of corresponding enantiomers, and A>B)

High Performance Liquid Chromatographic Analysis Conditions

Analysis of Conversion Rate

Column: YMC-A303 (4.6 mmφ×250 mm, manufactured by YMC Inc.), Eluent: 20 mM phosphoric acid aqueous solution (pH 2.5)/acetonitrile=9/1, Flow rate: 1.0 ml/minute, Column temperature: 30° C., Measuring wavelength: 210 nm Analysis of Optical Purity Column: CHIRALPAK AD-RH (4.6 mmφ×150 mm, manufactured by Daicel Chemical Industries, Ltd.), Eluent: 20 mM phosphate buffer (pH 8.0)/acetonitrile=7/3, Flow rate: 0.5 ml/minute, Column temperature: room temperature, Measuring wavelength: 210 nm extract 0.3%, yeast extract 0.3%, isovaleronitrile 0.1%, pH 7.0) sterilized in a Sakaguchi flask, and stirred and cultivated at 30° C. for 72 hours. After completion of the cultivation, the bacterial cells were collected by centrifugal separation, and suspended in 100 mM phosphate buffer (pH 7.0) to obtain a 20-fold concentrated bacterial cell suspension. To the bacterial cell suspension (100 ml), racemic 1-benzylnipecotamide (5 g) was added. The pH of the solution was adjusted to 7 using NaOH, and then the mixture was shaken at 30° C. for 60 hours. After completion of the reaction, solid substance such as bacterial cells was removed by centrifugal separation from the reaction mixture, and the pH of the mixture was adjusted to 10.0 using NaOH. The mixture was stirred at room temperature for 1 hour, and then precipitated crystal was filtrated to obtain 2.4 g of (R)-1-benzylnipecotamide. The compound was analyzed by the method of Example 1; as a result, the optical purity was 99.8% ee.

Example 3

Selective Hydrolysis of R-Enantiomer in Racemic Nipecotamide

*Cupriavidus* sp. KNK-J915 strain (FERM BP-10739) was cultivated by the method of Example 1 to prepare a bacterial cell suspension. The bacterial cell suspension (0.1 ml) was

TABLE 1

| Strain name | Conversion rate (%) | Substrate Optical purity (% ee) | Product Optical purity (% ee) |
|---|---|---|---|
| *Achromobacter xylosoxidans* subsp. *xylosoxidans* NBRC 13495 | 48.8 | 95.3 | 97.8 |
| *Cupriavidus* sp. KNK-J915 FERM BP-10739 | 52.0 | 99.9 | 92.3 |
| *Pseudomonas chlororaphis* NBRC3904 | 66.8 | 95.9 | 47.6 |
| *Rhodococcus erythropolis* IAM 1440 | 51.0 | 97.9 | 93.9 |

TABLE 2

| Strain name | Conversion rate (%) | Substrate Optical purity (% ee) | Product Optical purity (% ee) |
|---|---|---|---|
| *Brevibacterium iodinum* NBRC 3558 | 69.7 | 98.0 | 42.6 |
| *Pseudomonas fragi* NBRC 3458 | 59.4 | 97.2 | 66.3 |
| *Pectobacterium carotovorum* subsp. *carotovorum* NBRC12380 | 57.1 | 98.2 | 73.7 |
| *Staphylococcus epidermidis* JCM2414 | 52.2 | 92.6 | 84.7 |

Example 2

Method for producing (R)-1-benzylnipecotamide

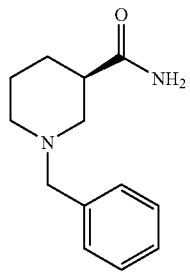

*Cupriavidus* sp. KNK-J915 stain (FERN BP-10739) was inoculated in a medium (glycerol 1.0%, peptone 0.5%, malt mixed with 100 mM phosphate buffer containing 1.0 to 5.0% of racemic nipecotamide (0.1 ml, pH 7.0), and the mixture was shaken at 30° C. for 35 hours. After completion of the reaction, solid substance such as bacterial cells was removed by centrifugal separation, and then a substrate and a product in the reaction mixture were reacted with benzyl chlorocarbonate for derivatization. The resulting derivative was analyzed by high performance liquid chromatography to determine the conversion rate (%) and optical purity (ee %). The results are listed in Table 3.

High Performance Liquid Chromatographic Analysis Conditions

Analysis of Conversion Rate

Column: YMC-A303 (4.6 mmφ×250 mm, manufactured by YMC Inc., Eluent: 20 mM phosphoric acid aqueous solution (pH 2.5)/acetonitrile=7/3, Flow rate: 1.0 ml/minute, Column temperature: 35° C., Measuring wavelength: 210 nm Analysis of Optical Purity Column: CHIRALPAK AD-RH (4.6 mmϕ×150 mm, manufactured by Daicel Chemical Industries, Ltd.), Eluent: 20 mM phosphate buffer (pH 2.5)/acetonitrile=7/3, Flow rate: 0.5 ml/minute, Column temperature: room temperature, Measuring wavelength: 210 nm

TABLE 3

| Concentration of racemic nipecotamide | Conversion rate (%) | Substrate Optical purity (% ee) | Product Optical purity (% ee) |
| --- | --- | --- | --- |
| 1.0 | 66.8 | 95.9 | 47.6 |
| 3.0 | 64.8 | 98.7 | 53.7 |
| 5.0 | 57.1 | 98.2 | 73.7 |

Example 4

Selective Hydrolysis of S-enantiomer in Racemic Nipecotamide

*Cupriavidus* sp. KNK-J915 strain (FERM BP-10739) was cultivated by the method of Example 2 to obtain a 20-fold concentrated bacterial cell suspension. To the bacterial cell suspension (100 ml), racemic nipecotamide (19.9 g) was added. After the pH of the mixture was adjusted to 7 using NaOH, the mixture was shaken at 30° C. for 60 hours. After completion of the reaction, the reaction mixture was heat-treated at 70° C. for 30 minutes, and solid substance such as bacterial cells was removed by centrifugal separation. The substrate and product in the reaction mixture were analyzed by the method of Example 3; as a result, the conversion rate was 52.7%, the optical purity of (R)-nipecotamide was 98.8% ee and the optical purity of (S)-nipecotamide was 88.1% ee.

Example 5

Method for producing (R)-1-(tert-butoxycarbonyl)nipecotamide

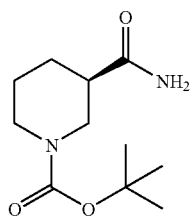

To the reaction mixture obtained in Example 4, THF (40 ml) was added, and di-tert-butyl dicarbonate (37.2 g, 2.3 equivalents) was added thereto. The pH of the reaction mixture was adjusted to 10.0 using NaOH. The reaction mixture was stirred for 1 hour at room temperature, and then the precipitated crystal was filtered off to obtain (R)-1-(tert-butoxycarbonyl)nipecotamide as white crystal (15.6 g, yield: 93%). The crystal was analyzed by the method of Example 3; as a result, the optical purity was 99.8% ee.

$^1$H NMR (400 MHz, CDCl$_3$): δ5.36 (brs, 2H), 3.94-3.08 (m, 5H), 1.96-1.36 (m, 13H)

Example 6

Method for producing (R)-1-(tert-butoxycarbonyl)nipecotamide

To the reaction mixture obtained in Example 4, THF (40 ml) was added, and di-tert-butyl dicarbonate (16.1 g, 1.0 equivalent) was added thereto. The pH of the reaction mixture was kept to 7.0 to 8.0. The reaction mixture was stirred for 3 hours at room temperature to obtain a solution containing (R)-1-(tert-butoxy carbonyl)nipecotamide (15.6 g, yield: 93%).

Example 7

Method for producing (R)-1-(tert-butoxycarbonyl)nipecotamide

To the reaction mixture obtained in Example 4, THF (40 ml) was added, and di-tert-butyl dicarbonate (16.1 g, 1.0 equivalent) was added thereto. The pH of the reaction mixture was kept to 5.0 to 6.0. The reaction mixture was stirred for 3 hours at room temperature to obtain a solution containing (R)-1-(tert-butoxy carbonyl)nipecotamide (3.5 g, yield: 21%).

Example 8

Method for producing (R)-1-(tert-butoxycarbonyl)nipecotamide

To the reaction mixture obtained in Example 4, THF (40 ml) was added, and di-tert-butyl dicarbonate (16.1 g, 1.0 equivalent) was added thereto. The pH of the reaction mixture was kept 5.0 to 7.0. The reaction mixture was stirred for 2 hours at room temperature to obtain a solution containing (R)-1-(tert-butoxycarbonyl) nipecotamide (1.9 g, yield: 11%).

Example 9

Method for producing (R)-1-(tert-butoxycarbonyl)nipecotamide

To the reaction mixture obtained in Example 4, tert-butyl dicarbonate (16.1 g, 1.0 equivalent) was added. The pH of the reaction mixture was kept from 7.0 to 8.0. The reaction mixture was stirred for 3 hours at room temperature to obtain a solution containing (R)-1-(tert-butoxycarbonyl)nipecotamide (6.6 g, yield: 39%).

Example 10

Method for producing (R)-1-benzoylnipecotamide

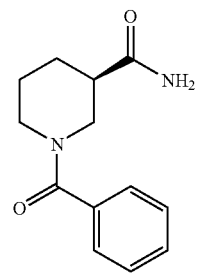

Concentrated sulfuric acid is added to the reaction mixture obtained in Example 4 (amount: 10 g, net weight of (R)-nipecotamide: 1 g) to adjust the pH to 9. Benzoyl chloride (3.5 g, 2.5 equivalents) was slowly added dropwise, and the pH of the reaction mixture was kept from 7 to 9 by a 30% aqueous sodium hydroxide solution. After completion of the dropwise addition, the solution was stirred at 15° C. for 3 hours to obtain a solution containing the title compound (1.6 g, yield: 88%).

$^1$H NMR (400 MHz, CDCl$_3$): δ7.45-7.36(m, 5H), 6.70 (brs, 2H), 5.56(brd, 1H), 4.17-3.75(m, 2H), 3.56-3.25(m, 2H), 2.18-1.88(m, 2H), 1.64-1.38(m, 2H)

Example 11

Method for producing
(R)-1-(p-methylbenzoyl)nipecotamide

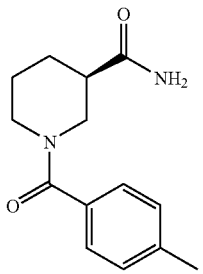

Concentrated sulfuric acid is added to the reaction mixture obtained in Example 4 (amount: 30 g, net weight of (R)-nipecotamide: 3 g) to adjust the pH to 9. To the mixture, p-Methylbenzoyl chloride (8.0 g, 2.2 equivalents) was slowly added dropwise, and the pH of the reaction mixture was kept from 7 to 9 by a 30% aqueous sodium hydroxide solution. After completion of the dropwise addition, the solution was stirred at 15° C. for 3 hours and the precipitated crystal was filtered off. The crystal was dried under reduced pressure to obtain the title compound as white crystal (4.4 g, yield: 760).

$^1$H NMR (400 MHz, CDCl$_3$): δ7.42-7.22(m, 4H), 6.56 (brs, 2H), 5.60(brd, 1H), 4.18-3.18(m, 4H), 2.18-1.40(m, 4H)

Example 12

Method for producing
(R)-1-(p-chlorobenzoyl)nipecotamide

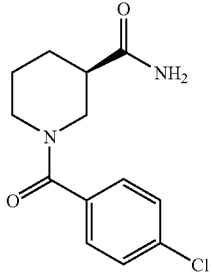

Concentrated sulfuric acid is added to the reaction mixture obtained in Example 4 (amount: 30 g, net weight of (R)-nipecotamide: 3 g) to adjust the pH to 9. To the mixture, p-Methylbenzoyl chloride (9.0 g, 2.2 equivalents) was slowly added dropwise, and the pH of the reaction mixture was kept from 7 to 9 by a 30% aqueous sodium hydroxide solution. After completion of the dropwise addition, the solution was stirred at 15° C. for 3 hours, and the precipitated crystal was filtered off. The crystal was dried under reduced pressure to obtain the title compound as white crystal (6.2 g, yield: 99%).

$^1$H NMR (400 MHz, CDCl$_3$): δ7.50-7.22(m, 4H), 6.68 (brd, 2H), 5.80(brs, 1H), 4.18-3.36(m, 4H), 2.60-1.46(m, 7H)

Example 13

Method for producing
(R)-1-(p-methylbenzoyl)-3-amino piperidine

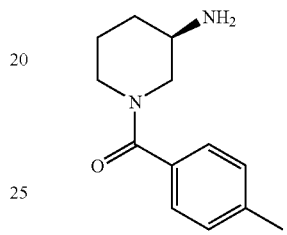

To the white crystal (4.0 g) obtained in Example 11, water (20 ml), sodium hydroxide (1.3 g, 2 equivalents) and aqueous sodium hypochlorite solution (10.2 g, 1 equivalent) were added. The mixture was stirred at 15 to 40° C. for 2 hours to obtain a pale yellow aqueous solution (34.7 g). To 11.0 g of the subdivided solution, isopropanol (5 ml) and sodium chloride (1 g) were added. The mixture was stirred at 60° C. for 10 minutes. The water layer was separated, and the solvent was evaporated under reduced pressure to obtain the title compound as yellow oil (0.72 g, yield: 64%).

$^1$H NMR (400 MHz, CDCl$_3$): δ7.42-7.18(m, 4H), 4.58-4.22(m, 1H), 3.84-3.46(m, 1H), 3.08-2.66(m, 3H), 2.44-1.24 (m, 7H)

Example 14

Method for producing
(R)-1-(p-chlorobenzoyl)-3-amino piperidine

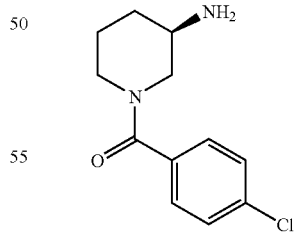

To the white crystal (5.7 g) obtained in Example 11, water (30 ml), sodium hydroxide (1.7 g, 2 equivalents) and aqueous sodium hypochlorite solutions (13.4 g, 1 equivalent) were added. The mixture was stirred at 15 to 40° C. for 2 hours to obtain a pale yellow aqueous solution (54.1 g). To 10.3 g of the subdivided solution, isopropanol (5 ml) and sodium chloride (1 g) were added. The mixture was stirred at 60° C. for 10 minutes. The water layer was removed, and the solvent was evaporated under reduced pressure to obtain the title compound as yellow oil (0.87 g, yield: 90%).

$^1$H NMR (400 MHz, CDCl$_3$): δ7.42-7.18(m, 4H), 4.52-4.16(m, 1H), 3.80-3.18(m, 1H), 3.06-2.64(m, 3H), 2.18-1.22(m, 4H)

Example 15

Method for producing (R)-1-(p-methylbenzoyl)-3-(benzoylamino)piperidine

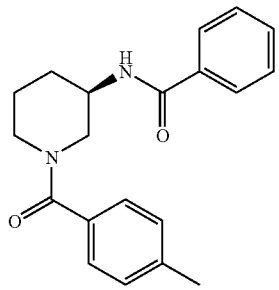

Benzoyl chloride (0.15 g) was added to the aqueous solution of (R)-1-(p-methylbenzoyl)-3-aminopiperidine obtained in Example 13 (amount: 3 g), and the pH of the mixture was kept from 8.0 to 9.0 using sodium hydroxide. The mixture was stirred at 15° C. for 3 hours. Chlorobenzene (3 ml) and sodium chloride (0.5 g) were added thereto, and then the mixture was stirred at 90° C. for 10 minutes. The water layer was removed, and the solvent was evaporated under reduced pressure to obtain the title compound as yellow crystal (0.33 g, yield: 73%).

$^1$H NMR (400 MHz, CDCl$_3$): δ7.58-7.14(m, 9H), 4.22 (brs, 1H), 3.60(brs, 1H), 2.37(s, 3H), 2.28-1.52(m, 4H)

Example 16

Method for producing (R)-1-(p-chlorobenzoyl)-3-(benzoylamino)piperidine

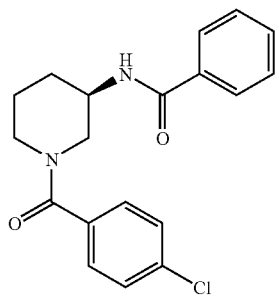

Benzoyl chloride (0.15 g) was added to the aqueous solution of (R)-1-(p-chlorobenzoyl)-3-aminopiperidine obtained in Example 14 (amount: 3 g), and the pH of the mixture was kept from 8.0 to 9.0 using sodium hydroxide. The mixture was stirred at 15° C. for 3 hours, and chlorobenzene (3 ml) and sodium chloride (0.5 g) were added thereto. The mixture was stirred at 90° C. for 10 minutes. The water layer was removed, and the solvent was evaporated under reduced pressure to obtain the title compound as yellow crystal (0.42 g, yield: 100%).

$^1$H NMR (400 MHz, CDCl$_3$): δ7.90-7.16(m, 9H), 6.04 (brs, 1H), 4.32-3.18(m, 5H), 2.18-1.40(m, 4H)

Example 17

Method for producing (R)-1-(p-methylbenzoyl)-3-(p-methylbenzoylamino)piperidine

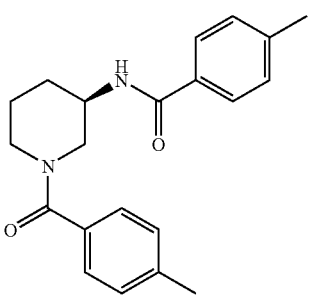

To the aqueous solution of (R)-1-(p-methylbenzoyl)-3-amino piperidine obtained in Example 13 (amount: 3 g), p-Methylbenzoyl chloride (0.16 g) was added. The pH of the mixture was kept from 8.0 to 9.0 using sodium hydroxide. The mixture was stirred at 15° C. for 3 hours, and the precipitated crystal was filtered off. The crystal was dried under reduced pressure to obtain the title compound as white crystal (0.28 g, yield: 59%).

$^1$H NMR (400 MHz, CDCl$_3$): δ7.82-7.12(m, 8H), 6.12 (brs, 1H), 4.21(s, 2H), 3.59(s, 2H), 3.35(s, 1H), 2.39(s, 3H), 2.36 (s, 3H), 2.10-1.40(m, 4H)

Example 18

Method for producing (R)-1-(p-chlorobenzoyl)-3-(p-methylbenzoylamino)piperidine

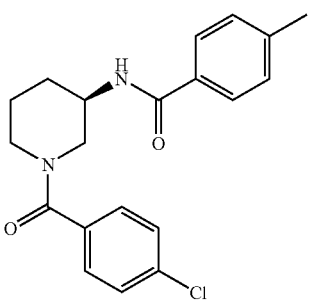

To the aqueous solution of (R)-1-(p-chlorobenzoyl)-3-amino piperidine obtained in Example 14 (amount: 3 g), p-Methylbenzoyl chloride (0.16 g) was added. The pH of the mixture was kept from 8.0 to 9.0 using sodium hydroxide. The mixture was stirred at 15° C. for 3 hours, and the precipitated crystal was filtered off. The crystal was dried under reduced pressure to obtain the title compound as white crystal (0.28 g, yield: 66%).

$^1$H NMR (400 MHz, CDCl$_3$): δ7.80-7.16(m, 8H), 6.08 (brs, 1H), 4.36-3.12(m, 5H), 2.40(s, 3H), 2.22-1.42(m, 4H)

Example 19

Method for producing (R)-1-(p-methylbenzoyl)-3-(p-chlorobenzoylamino)piperidine

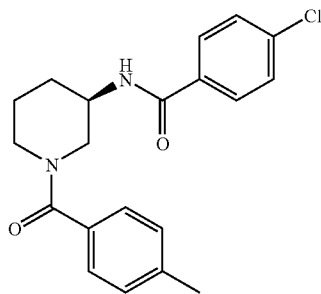

To the aqueous solution of (R)-1-(p-methylbenzoyl)-3-amino piperidine obtained in Example 13 (amount: 3 g), p-chlorobenzoyl chloride (0.18 g) was added. The pH of the mixture was kept from 8.0 to 9.0 using sodium hydroxide. The mixture was stirred at 15° C. for 3 hours, and chlorobenzene (3 ml) and sodium chloride (0.5 g) were added thereto. The mixture was stirred at 90° C. for 10 minutes. The water layer was removed, and the solvent was evaporated under reduced pressure to obtain the title compound as yellow crystal (0.42 g, yield: 84%).

$^1$H NMR (400 MHz, CDCl$_3$): δ7.88-7.08(m, 8H), 4.21 (brs, 1H), 3.82-3.18(m, 3H), 2.37(s, 3H), 2.16-1.42(m, 4H)

Example 20

Method for producing (R)-1-(p-chlorobenzoyl)-3-(p-chlorobenzoylamino) piperidine

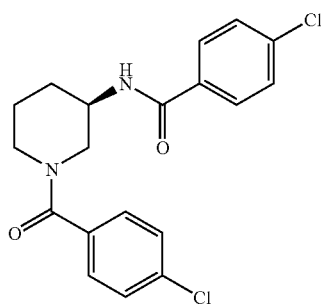

To the aqueous solution of (R)-1-(p-chlorobenzoyl)-3-amino piperidine obtained in Example 14 (amount: 3 g), p-chlorobenzoyl chloride (0.15 g) was added. The pH of the mixture was kept from pH 8.0 to 9.0 using sodium hydroxide. The mixture was stirred at 15° C. for 3 hours, and chlorobenzene (3 ml) and sodium chloride (0.5 g) were added. The mixture was stirred at 90° C. for 10 minutes. The water layer was removed, and the solvent was evaporated under reduced pressure to obtain the title compound as yellow crystal (0.16 g, yield: 36%).

$^1$H NMR (400 MHz, CDCl$_3$): δ7.82-7.20(m, 8H), 6.02 (brs, 1H), 4.36-3.08(m, 5H), 2.22-1.22(m, 4H)

Example 21

Method for producing (R)-1-(p-methylbenzoyl)-3-(tert-butoxycarbonylamino)piperidine

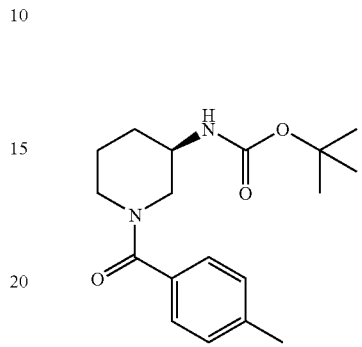

Potassium carbonate (0.15 g) and di-tert-butyl dicarbonate (0.23 g) were added to the aqueous solution of (R)-1-(p-methyl benzoyl)-3-aminopiperidine obtained in Example 13 (amount: 3 g). The mixture was stirred at 15° C. for 3 hours, and chlorobenzene (3 ml) and sodium chloride (0.5 g) were added. The mixture was stirred at 90° C. for 10 minutes. The water layer was removed, and the solvent was evaporated under reduced pressure to obtain the title compound as yellow oil (0.31 g, yield: 69%).

$^1$H NMR (400 MHz, CDCl$_3$): δ7.38-7.18(m, 4H), 4.68 (brs, 1H), 3.80-3.06(m, 4H), 2.36(s, 3H), 1.98-1.26(m, 13H)

Example 22

Method for producing (R)-1-(p-chlorobenzoyl)-3-(tert-butoxycarbonylamino)piperidine

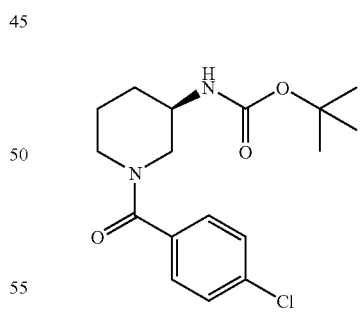

Potassium carbonate (0.15 g) and di-tert-butyl dicarbonate (0.23 g) were added to the aqueous solution of (R)-1-(p-chloro benzoyl)-3-aminopiperidine obtained in Example 14 (amount: 3 g). The mixture was stirred at 15° C. for 3 hours, and the precipitated crystal was filtered off. The crystal was dried under reduced pressure to obtain the title compound as white crystal (0.35 g, yield: 87%).

$^1$H NMR (400 MHz, CDCl$_3$): δ7.43-7.28(m, 4H), 4.57 (brs, 1H), 3.82-3.02(m, 4H), 1.98-1.22(m, 13H)

Example 23

Method for producing (R)-1-(p-methylbenzoyl)-3-(benzyloxycarbonylamino)piperidine

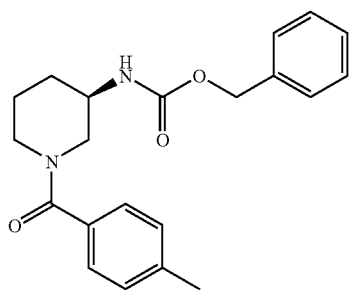

Potassium carbonate (0.15 g) and benzyl chlorocarbonate (0.18 g) were added to the aqueous solution of (R)-1-(p-methylbenzoyl)-3-aminopiperidine obtained in Example 13 (amount: 3 g). The mixture was stirred at 15° C. for 3 hours, and chlorobenzene (3 ml) and sodium chloride (0.5 g) were added. The mixture was stirred at 90° C. for 10 minutes. The water layer was removed, and the solvent was evaporated under reduced pressure to obtain the title compound as yellow oil (0.36 g, yield: 73%).

$^1$H NMR (400 MHz, CDCl$_3$): δ7.46-7.20(m, 9H), 5.22-4.82 (m, 3H), 3.98-3.02(m, 5H), 2.00-1.40(m, 4H)

Example 24

Method for producing (R)-1-(p-chlorobenzoyl)-3-(benzyloxycarbonylamino)piperidine

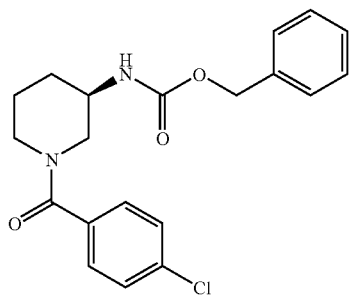

Potassium carbonate (0.15 g) and benzyl chlorocarbonate (0.18 g) were added to the aqueous solution of (R)-1-(p-chlorobenzoyl)-3-aminopiperidine obtained in Example 14 (amount: 3 g). The mixture was stirred at 15° C. for 3 hours, and chlorobenzene (3 ml) and sodium chloride (0.5 g) were added. The mixture was stirred at 90° C. for 10 minutes. The water layer was removed, and the solvent was evaporated under reduced pressure to obtain the title compound as yellow oil (0.16 g, yield: 35%).

$^1$H NMR (400 MHz, CDCl$_3$): δ7.46-7.20(m, 9H), 5.22-4.82(m, 3H), 3.98-3.02(m, 5H), 2.00-1.40(m, 4H)

Example 25

Method for producing (R)-1-benzoyl-3-aminopiperidine

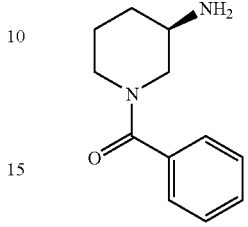

Sodium hydroxide (7.4 g, 2 equivalents) and sodium hypochlorite (64.0 g, 1.1 equivalents) were added to the aqueous solution of (R)-1-benzoyl nipecotamide obtained in the method described in Example 10 (amount: 210 g, net weight: 20.8 g). The mixture was stirred at 25° C. for 6 hours to obtain a solution (280.90 g) containing the title compound (17.7 g, yield: 97%).

$^1$H NMR (400 MHz, CDCl$_3$): δ7.50-7.35(m, 5H), 3.78-3.50(m, 1H), 3.04-2.64(m, 4H), 2.06-1.24(m, 4H)

Example 26

Method for producing (R)-1-benzoyl-3-(benzoylamino) piperidine

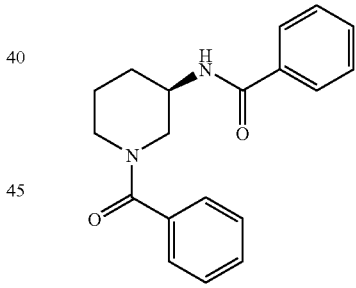

Concentrated hydrochloric acid is added to the solution obtained by the method described in Example 25, and the pH of the mixture was adjusted to 9. Chlorobenzene (100 ml) is added to the mixture, and benzoyl chloride (19.9 g, 1.5 equivalents) is added slowly thereto. The pH of the mixture was adjusted to from 7.0 to 9.0 using a 30% aqueous sodium hydroxide solution. The mixture was stirred at 15° C. for 2 hours, and the temperature was raised to 90° C., and then the mixture was stirred for 30 minutes. The aqueous layer was separated, and the organic layer was washed with an aqueous sodium bicarbonate solution (20 ml). The organic layer was concentrated under reduced pressure, and the precipitated crystal was filtered off to obtain the title compound as white crystal (22.7 g, yield: 84%).

$^1$H NMR (400 MHz, CDCl$_3$): δ8.19-7.26(m, 10H), 6.18 (brs, 1H), 4.38-3.23(m, 5H), 2.32-1.48(m, 4H)

Example 27

Method for producing (R)-3-aminopiperidine dihydrochloride

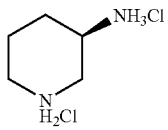

The crystal (21.2 g) obtained by the method described in Example 26 was mixed with 6 N hydrochloric acid (160 ml), and the mixture was stirred at 100° C. for 14 hours. The internal temperature was cooled to 70° C., and the mixture was washed with toluene (50 ml). The water layer was concentrated under reduced pressure, and isopropanol (50 ml) was added to the concentrated mixture, and the mixture was further concentrated under reduced pressure. The resulting white solid was dissolved in methanol (60 ml), and then ethyl acetate (60 ml) was slowly added thereto. The precipitated crystal was filtered off, and the title compound (10.8 g, yield: 92%, 99.5% ee) was obtained as white crystal.

$^1$H NMR (400 MHz, $D_2O$): δ3.70(d, 1H), 3.63(tt, 1H), 3.46(d, 1H), 3.11-2.97(m, 2H), 2.26(brd, 1H), 2.12(brd, 1H), 1.90-1.66(m, 2H)

Example 28

Method for producing (R)-1-(tert-butoxycarbonyl)-3-aminopiperidine

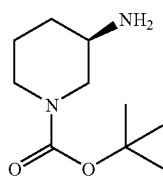

To a solution (amount 9 g) of (R)-1-(tert-butoxy carbonyl) nipecotamide (net weigh of (R)-1-(tert-butoxycarbonyl) nipecotamide: 0.7 g), Sodium hydroxide (1.3 g, 10 equivalents) and an aqueous sodium hypochlorite solution (2.2 g, 1.1 equivalents) were added. The mixture was stirred at 15 to 25° C. for 16 hours. The water layer was removed, and the solvent was evaporated under reduced pressure. Toluene (10 ml) and saturated brine (5 ml) were added thereto, and the water layer was removed. The solvent was evaporated under reduced pressure to obtain the title compound as yellow oil (0.7 g, net weight: 0.5 g, yield: 80%).

Example 29

Method for producing (R)-3-aminopiperidine dihydrochloride

In isopropanol (3 ml), (R)-1-(tert-butoxycarbonyl)-3-amino piperidine (0.5 g) obtained by the method described in Example 28 was dissolved. The solution was slowly added dropwise into a 28% hydrogen chloride/isopropanol solution (5 ml), and the mixture was stirred for 3 hours after completion of dropwise addition. The precipitated crystal was filtered off to obtain the title compound as white crystal (0.4 g, yield: 98%).

Example 30

Method for producing (R)-1-benzoyl-(p-methylbenzoyl amino)piperidine

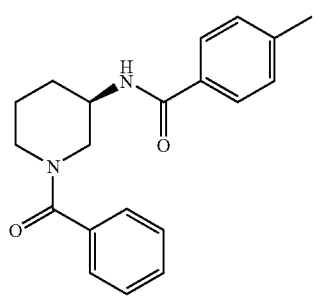

To an aqueous solution of (R)-1-benzoylaminopiperidine (amount: 1.6 g, net weight of (R)-1-benzoylamino piperidine: 0.16 g) obtained by the method described in Example 25, p-methylbenzoyl chloride (0.12 g, 1.5 equivalents) was slowly added The pH of the mixture was adjusted to from 7.0 to 9.0 using an 30% aqueous sodium hydroxide solution. The mixture was stirred at 15° C. for 5 hours, and then the precipitated crystal was filtered off to obtain the title compound as white crystal (0.20 g, yield: 78%).

$^1$H NMR (400 MHz, $CDCl_3$): δ7.80-7.05(m, 9H), 6.06 (brs, 1H), 4.30-3.20(m, 5H), 2.40(s, 3H), 2.32-1.46(m, 4H)

Example 31

Method for producing (R)-1-benzoyl-3-(p-chloro benzoylamino)piperidine

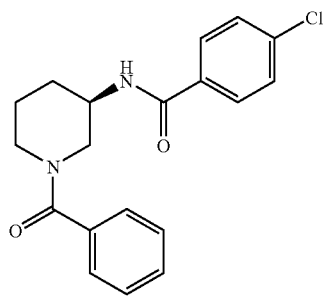

To an aqueous solution of (R)-1-benzoylaminopiperidine (amount: 1.6 g, net weight of (R)-1-benzoylamino piperidine: 0.16 g) obtained by the method described in Example 25, p-chlorobenzoyl chloride (0.14 g, 1.5 equivalents) was slowly added. The pH of the mixture was adjusted to from 7.0 to 9.0 using a 30% aqueous sodium hydroxide solution. The mixture was stirred at 15° C. for 5 hours, and then the precipitated crystal was filtered off to obtain the title compound as white crystal (0.25 g, yield: 92%).

$^1$H NMR (400 MHz, $CDCl_3$): δ7.88-7.26(m, 9H), 6.20 (brs, 1H), 4.30-3.22(m, 5H), 2.36-1.44(m, 4H)

Example 32

Method for producing (R)-1-benzoyl-3-(benzoylamino) piperidine

Concentrated hydrochloric acid is added to the solution obtained by the method described in Example 25 to adjust the pH to pH 9. Chlorobenzene (100 ml) is added thereto, and benzoyl chloride (19.9 g and 1.5 equivalents) is added slowly thereto, and then the pH of the mixture was adjusted to from 7.0 to 9.0 using a 30% aqueous sodium hydroxide solution. The mixture was stirred at 15° C. for 6 hours, and then the precipitated crystal was filtered off to obtain the title compound as white crystal (25.1 g, yield: 93%).

Example 33

Method for producing (R)-1-(benzyl)-3-amino piperidine

In (R)-1-(benzyl)nipecotamide (1.1 g) produced by the method described in Example 2, water (5 ml), a 30% aqueous sodium hydroxide solution (6.7 g, 10 equivalents), THF (10 ml), an aqueous sodium hypochlorite solution (11.2 g, 1.5 equivalents) were mixed. The mixture was stirred at 15° C. for 1 hour and at 60° C. for 2 hours. The mixture was cooled to 20° C., and extracted with toluene (10 ml) three times. After the organic layers were combined, the combined organic layer was concentrated under reduced pressure to obtain the title compound as yellowish brown oil (0.8 g, yield: 55%).

Example 34

Method for producing (R)-3-aminopiperidine dihydrochloride

To (R)-1-(benzyl)-3-aminopiperidine (pure amount: 18.9 g) produced by the method described in Example 33, methanol (190 ml), concentrated hydrochloric acid (24.7 g, 2.5 equivalents) and 10 wt % Pd/C (1.9 g) were added sequentially. The air in the reactor vessel was substituted by hydrogen. The mixture was stirred at 40° C. for 24 hours, and the catalyst was filtrated. The filtrate was concentrated under reduced pressure to obtain the title compound as white crystal (21.5 g, yield: 99%).

The invention claimed is:

1. A method for producing an optically active nipecotamide derivative or an optically active nipecotin derivative, comprising a step of:

stereoselectively hydrolyzing a racemic nipecotamide derivative represented by the following formula (1):

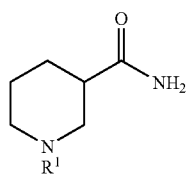

(1)

wherein, $R^1$ represents a hydrogen atom or a benzyl group, by using an enzyme source having an ability to stereoselectively hydrolyze the racemic nipecotamide derivative (1), to produce an optically active nipecotamide derivative represented by the following formula (2):

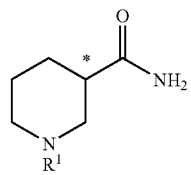

(2)

wherein, * indicates an asymmetric carbon atom; and $R^1$ means the same as the above, and an optically active nipecotin derivative represented by the following formula (3):

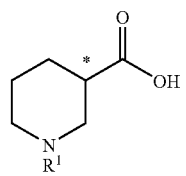

(3)

wherein, * and $R^1$ mean the same as the above, and wherein, the enzyme source having the ability to stereoselectively hydrolyze the racemic nipecotamide derivative (1) is derived from a microorganism belonging to genus Achromobacter, Cupriavidus, Pectobacterium or Staphylococcus;

from the racemic nipecotamide derivative (1).

2. The production method according to claim 1, wherein the enzyme source is derived from a microorganism belonging to genus Achromobacter or Cupriavidus, and has an ability to stereoselectively hydrolyze an S-enantiomer in the racemic nipecotamide derivative (1), for producing an R-enantiomer of the optically active nipecotamide derivative (2) or an S-enantiomer of the optically active nipecotin derivative (3).

3. The production method according to claim 2, wherein the enzyme source is derived from a microorganism selected from the group consisting of Achromobacter xylosoxidans subsp. xylosoxidans and Cupriavidus sp.

4. The production method according to claim 1, wherein the enzyme source is derived from a microorganism belonging to genus Pectobacterium or Staphylococcus, and has an ability to stereoselectively hydrolyze an R-enantiomer in the racemic nipecotamide derivative (1), for producing an S-enantiomer of the optically active nipecotamide derivative (2) or an R-enantiomer of the optically active nipecotin derivative (3).

5. The production method according to claim 4, wherein the enzyme is derived from a microorganism selected from the group consisting of Pectobacterium carotovorum subsp. carotovorum and Staphylococcus epidermidis.

6. The production method according to claim 1, wherein $R^1$ represents a hydrogen atom in the formulae (1), (2) and (3).

7. The production method according to claim 6, further comprising selectively protecting the optically active nipecotamide (2) with a tert-butoxycarbonyl group to produce optically active 1-(tert-butoxycarbonyl) nipecotamide represented by the following formula (8):

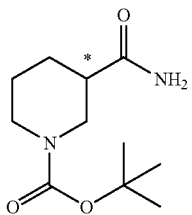

(8)

wherein, * indicates an asymmetric carbon atom.

8. The production method according to claim 7, wherein selectively protecting optically active nipecotamide (2) comprises reacting the optically active nipecotamide (2) with di-tert-butyl dicarbonate in a two layer-mixture consisting of an organic solvent and water at a pH of not less than 7.

9. The production method according to claim 7, further comprising rearranging the optically active 1-(tert-butoxycarbonyl)nipecotamide (8) by Hofmann rearrangement to produce optically active 1-(tert-butoxycarbonyl)-3-aminopiperidine or a salt thereof represented by the following formula (9):

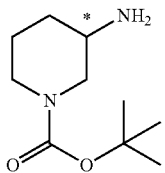

(9)

wherein, * means the same as the above,
and deprotecting the optically active 1-(tert-butoxycarbonyl)-3-aminopiperdine (9) or salt thereof to produce optically active 3-aminopiperdine or salt thereof represented by the following formula (7):

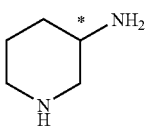

(7)

wherein, * means the same as the above.

10. The production method according to claim 6, further comprising aroylating the optically activated nipecotamide (2) to produce an optically active 1-aroylnipecotamide derivative represented by the following formula (4):

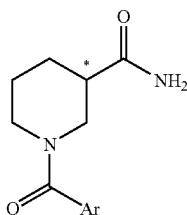

(4)

wherein, * indicates an asymmetric carbon atom; Ar represents an optionally substituted aryl group having 6 to 15 carbon atoms;

and then rearranging the optically active 1-aroylnipecotamide derivative (4) by Hofmann rearrangement to the amide group to produce an optically active 1-aroyl-3-aminopiperidine derivative represented by the following formula (5):

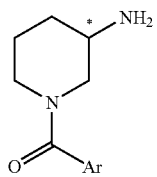

(5)

wherein, * and Ar mean the same as the above,
and then aroylating or carbamating the amino group of the optically active 1-aroyl-3-aminopiperidine derivative (5) for crystallization or extraction to isolate the optically active 1-aroyl-3-(protected amino)piperidine derivative represented by the following formula (6):

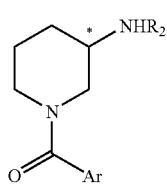

(6)

wherein, * and Ar mean the same as the above; $R^2$ represents an optionally substituted aroyl group having 7 to 15 carbon atoms, an alkyloxycarbonyl group having 2 to 15 carbon atoms, an alkenyloxycarbonyl group having 3 to 15 carbon atoms, an aryloxycarbonyl group having 7 to 15 carbon atoms, or an aralkyloxycarbonyl group having 8 to 15 carbon atoms.

11. The production method according to claims 10, further comprising hydrolyzing the compound (6) to produce optically active 3-aminopiperidine or salt thereof represented by the following formula (7):

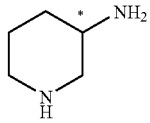

(7)

wherein, * means the same as the above.

12. The production method according to claim 10, wherein Ar represents a phenyl group, a p-methylphenyl group or a p-chlorophenyl group; $R^2$ represents a benzoyl group, a p-methylbenzoyl group, a p-chlorobenzoyl group, a tert-butoxycarbonyl group or a benzyloxycarbonyl group.

13. The production method according to claim 1, further comprising rearranging the optically active nipecotamide (2) which is the optically active 1-(benzyl)nipecotamide represented by the following formula (2″):

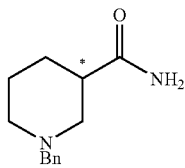

(2″)

wherein, * indicates an asymmetric carbon atom, by Hofmann rearrangement to produce an optically active 1-(benzyl)aminopiperidine or salt thereof represented by the following formula (10):

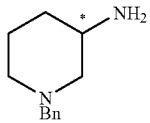

(10)

wherein, * means the same as the above;
and further removing the benzyl group of the optically active 1-(benzyl)aminopiperidine (10) or salt thereof to produce an optically active 3-aminopiperdine or salt thereof represented by the following formula (7):

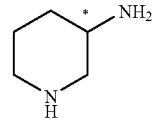

(7)

wherein, * indicates an asymmetric carbon atom.

* * * * *